United States Patent [19]

Berger et al.

[11] 4,388,467
[45] Jun. 14, 1983

[54] CYCLOALKA[4,5]PYRROLO[2,3-G]ISOQUINOLINES

[75] Inventors: Leo Berger, Montclair; Gary L. Olson, Westfield, both of N.J.

[73] Assignee: Hoffmann-La Roche Inc., Nutley, N.J.

[21] Appl. No.: 361,667

[22] Filed: Mar. 25, 1982

Related U.S. Application Data

[60] Division of Ser. No. 230,765, Feb. 2, 1981, Pat. No. 4,334,070, which is a continuation-in-part of Ser. No. 216,116, Dec. 15, 1980, abandoned, which is a continuation-in-part of Ser. No. 125,604, Feb. 28, 1980, abandoned.

[51] Int. Cl.³ .......................................... C07D 209/88
[52] U.S. Cl. .................................................. 548/439
[58] Field of Search ......................................... 548/439

[56] References Cited

U.S. PATENT DOCUMENTS 3,467,755  9/1969  Schoen et al. ..................... 548/439

Primary Examiner—Robert W. Ramsuer
Attorney, Agent, or Firm—Jon S. Saxe; Bernard S. Leon; William G. Isgro

[57] ABSTRACT

Neuroleptically active cycloalka[4,5]pyrrolo[2,3-g]isoquinolines of the formula

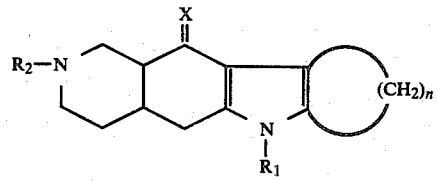

wherein n, $R_1$, $R_2$ and X are as hereinafter set forth, and intermediates therefore are described.

1 Claim, No Drawings

CYCLOALKA[4,5]PYRROLO[2,3-G]ISOQUINO-LINES

CROSS-REFERENCE TO RELATED APPLICATIONS

This is a division of application Ser. No. 230,765 filed Feb. 2, 1981 now U.S. Pat. No. 4,334,070, which is a continuation-in-part of U.S. patent application Ser. No. 216,116, filed Dec. 15, 1980, abandoned which in turn is a continuation-in-part of U.S. patent application Ser. No. 125,604, filed Feb. 28, 1980 abandoned.

BRIEF SUMMARY OF THE INVENTION

The invention relates to cycloalka[4,5]pyrrolo[2,3-g]isoquinolines of the formula

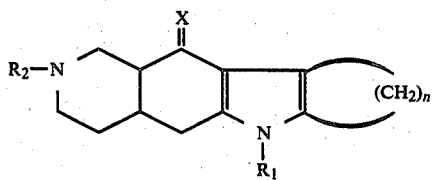

A wherein $R_1$ is hydrogen, alkyl, acyl or aralkyl; $R_2$ is hydrogen, alkyl, hydroxyalkyl, arylhydroxyalkyl, alkoxyalkyl, acyloxyalkyl, acylalkyl, aralkyl, alkenyl, cycloalkylalkyl, alkynyl, thienyl-alkyl, furyl-alkyl, arylcarboxamidoalkyl, aralkenyl, alkenyloxyalkyl, aryloxyalkyl, aralkyloxyalkyl, or aryl-N-imidazolonylalkyl; X is O or S; and n is 3, 4, 5 or 6,
and their pharmaceutically acceptable acid addition salts.

In yet another aspect, the invention relates to intermediates of the formula

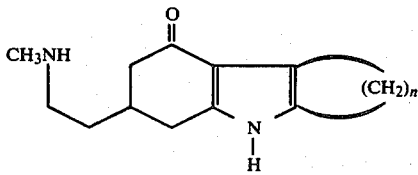

IXa wherein n is 3, 4, 5 or 6.

In still another aspect, the invention relates to intermediates of the formula

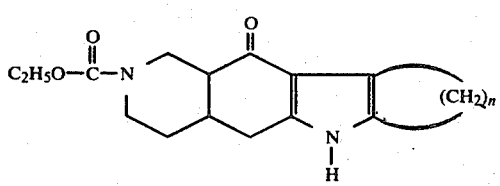

XIII

DETAILED DESCRIPTION OF THE INVENTION

The invention relates to cycloalka[4,5]pyrrolo[2,3-g]isoquinolines of the formula

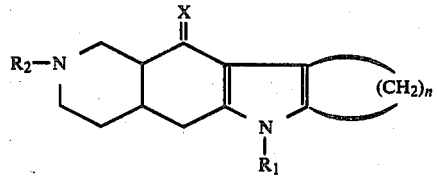

A wherein $R_1$ is hydrogen, alkyl, acyl or aralkyl; $R_2$ is hydrogen, alkyl, hydroxyalkyl, arylhydroxyalkyl, alkoxyalkyl, acyloxyalkyl, acylalkyl, aralkyl, alkenyl, cycloalkyl-alkyl, alkynyl, thienyl-alkyl, furyl-alkyl, arylcarboxamidoalkyl, aralkenyl, alkenyloxyalkyl, aryloxyalkyl, aralkyloxyalkyl, or aryl-N-imidazolonylalkyl; X is O or S; and n is 3, 4, 5 or 6,
and their pharmaceutically acceptable acid addition salts.

As used herein, the term "alkyl" preferably denotes "lower alkyl", which denotes a straight or branched chain saturated hydrocarbon containing 1 to 7 carbon atoms, for example, methyl, ethyl, propyl, isopropyl, butyl, t-butyl, neopentyl, pentyl, heptyl, and the like. The term "cycloalkyl" denotes a cyclic alkyl group of 3 to 6 carbon atoms, for example, cyclopropyl, cyclohexyl, and the like. The term "alkoxy", preferably denotes "lower alkoxy", which denotes an alkyl ether group in which the lower alkyl group is as described above, for example, methoxy, ethoxy, propoxy, pentoxy, and the like. The term "alkenyl" preferably denotes "lower alkenyl", which denotes a straight or branched chain unsaturated hydrocarbon containing 2 to 7 carbon atoms, for example, vinyl, allyl, and the like. The term "alkenyloxy", preferably denotes "lower alkenyloxy", which denotes an alkenyl ether group in which the lower alkenyl group is as described above, for example, ethenyloxy, and the like. The term "alkynyl" preferably denotes "lower alkynyl", which denotes a straight or branched chain unsaturated hydrocarbon containing 2 to 7 carbon atoms, for example, ethynyl, propargyl, methylbutynyl, and the like. The term "halogen" or "halo" denotes all the halogens, i.e., bromine, chlorine, fluorine, and iodine. The term "aryl" denotes phenyl or phenyl bearing one or more substituents selected from the group consisting of halogen, trifluoromethyl, lower alkyl, lower alkoxy, nitro, amino, lower alkylamino, and di-lower alkylamino. The term "aralkyl" preferably denotes an aryl group linked to an alkylene chain of 1 to 4 carbon atoms, such as, 2-phenylethyl, 4-chlorobenzyl, benzyl and the like. The term aralkenyl preferably denotes 3-phenyl-2-propenyl, and the like. The term "aralkyloxy" denotes an aralkyl ether, for example, benzyloxy, and the like. The term "aryloxy" denotes an aryl ether group in which the aryl group is as described above, for example, phenoxy, and the like. The term "acyl" denotes an "alkanoyl" group derived from an aliphatic carboxylic acid of 1 to 7 carbon atoms, for example, formyl, acetyl, propionyl, and the like; and an "aroyl" group derived from an aromatic carboxylic acid, such as benzoyl, 4-fluorobenzoyl and the like. The term "acyloxy" denotes an "alkanoyloxy" group derived from an aliphatic carboxylic acid of 1 to 7 carbon atoms, for example, formyloxy, acetoxy, propionyloxy, and the like; and an "aroyloxy" group derived from an aromatic carboxylic acid, such as benzoyloxy and the like. Exemplary of "acylalkyl" are 2-oxopropyl, 4-(4-fluorophenyl)-4 oxobutyl and the like. Exemplary of "acyloxyalkyl" are 2-acetoxyethyl, 3-benzoyloxypropyl and the like. Exemplary of "hydroxyalkyl" are hydroxyethyl, 2-hydroxy-3,3-dimethylbutyl and the like. Exemplary of "cycloalkyl-alkyl" are cyclopropylmethyl, cyclobutylmethyl and the like. Exemplary of "arylcarboxamidoalkyl" are benzamidoethyl and the like. Exemplary of "aryloxyalkyl" are 3-phenoxypropyl and the like. Exemplary of "aralkyloxyalkyl" are 2-benzyloxyethyl, 3-benzyloxypropyl and the like. Exemplary of "aryl-N-imidazolonylalkyl" are 2-(2,3-dihydro-2-oxo-1H-benzimidazol-1-yl)ethyl, 3-(2,3-dihydro-2-oxo-1H-benzimidazol-1-yl)propyl and the like. Exemplary of "arylhydroxyalkyl" are 2-hydroxy-2-phenylethyl, 2-hydroxy-2-(4-chlorophenyl)ethyl and the like. Exemplary of "alkoxyalkyl" are 2-ethoxyethyl, 3-methoxypropyl and the like. Exemplary of "alkenyloxyalkyl" are 2-ethenyloxyethyl and the like.

Preferred compounds of formula A are those wherein n is 3, 4, 5 or 6, $R_1$ is hydrogen, $R_2$ is alkyl, hydroxyalkyl, arylhydroxyalkyl, alkoxyalkyl, aryloxyalkyl, acylalkyl, or aralkyl; and X is O or S.

More preferred compounds of formula A are those wherein n is 3 or 4, $R_1$ is hydrogen, $R_2$ is alkyl, hydroxyalkyl, arylhydroxyalkyl, alkoxyalkyl, aryloxyalkyl, acylalkyl, or aralkyl; and X is O.

Most preferred compounds of formula A of the invention are:

2-methyl-1,2,3,4,4a,5,7,8,9,10a-decahydro-4a,10a-trans-6H-cyclopenta[4,5]pyrrolo[2,3-g]isoquinolin-10(10H)-one;

2-methyl-1,2,3,4,4a,5,7,8,9,10a-decahydro-4a,10a-trans-6H-cyclopenta[4,5]pyrrolo[2,3-g]isoquinolin-10(10H)-one hydrochloride, 0.5 molar hydrate;

2-(2-phenylethyl)-1,2,3,4,4a,5,7,8,9,10a-decahydro-4a,10a-trans-6H-cyclopenta[4,5]pyrrolo[2,3-g]isoquinolin-10(10H)-one;

2-[4-(4-fluorophenyl)-4-oxobutyl]-1,2,3,4,4a,5,7,8,9,10a-decahydro-4a,10a-trans-6H-cyclopenta[4,5]pyrrolo[2,3-g]isoquinolin-10(10H)-one;

(−)-2-methyl-1,2,3,4,4a,5,7,8,9,10a-decahydro-4a,10a-trans-6H-cyclopenta[4,5]pyrrolo[2,3-g]isoquinolin-10(10H)-one;

2-methyl-2,3,4,4a,5,7,8,9,10,11a-decahydro-4a,11a-trans-1H,6H-cyclohexa[4,5]pyrrolo[2,3-g]isoquinolin-11(11H)-one;

2-methyl-2,3,4,4a,5,7,8,9,10,11a-decahydro-4a,11a-trans-1H,6H-cyclohexa[4,5]pyrrolo[2,3-g]isoquinolin-11(11H)-one, 0.75 molar hydrate;

2-(2-phenylethyl)-2,3,4,4a,5,7,8,9,10,11a-decahydro-4a,11a-trans-1H,6H-cyclohexa[4,5]pyrrolo[2,3-g]isoquinolin-11(11H)-one;

2-[4-(4-fluorophenyl)-4-oxobutyl]-2,3,4,4a,5,7,8,9,10,11a-decahydro-4a,11a-trans-1H,6H-cyclohexa[4,5-]pyrrolo[2,3-g]isoquinolin-11(11H)-one; and 2-methyl-1,2,3,4,4a,5,7,8,9,10a-decahydro-4a,10a-trans-6H-cyclopenta[4,5]pyrrolo[2,3-g]isoquinolin-10(10H)-thione.

Exemplary of the compounds of formula A wherein n is 3, i.e., a compound of the formula

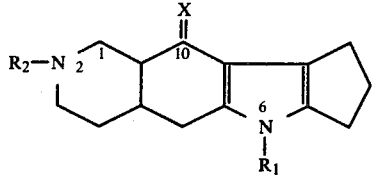

A-1 wherein $R_1$, $R_2$ and X are as previously described, are:

2-ethyl-1,2,3,4,4a,5,7,8,9,10a-decahydro-4a,10a-trans-6H-cyclopenta[4,5]pyrrolo[2,3-g]isoquinolin-10(10H)-one;

2-(2-hydroxyethyl)-1,2,3,4,4a,5,7,8,9,10a-decahydro-4a,10a-trans-6H-cyclopenta[4,5]pyrrolo[2,3-g]isoquinolin-10(10H)-one;

2-(2-hydroxy-2-phenylethyl)-1,2,3,4,4a,5,7,8,9,10a-decahydro-4a,10a-trans-6H-cyclopenta[4,5]pyrrolo[2,3-g]isoquinolin-10(10H)-one;

2-(2-ethoxyethyl)-1,2,3,4,4a,5,7,8,9,10a-decahydro-4a,10a-trans-6H-cyclopenta[4,5]pyrrolo[2,3-g]isoquinolin-10(10H)-one;

2-(2-acetoxyethyl)-1,2,3,4,4a,5,7,8,9,10a-decahydro-4a,10a-trans-6H-cyclopenta[4,5]pyrrolo[2,3-g]isoquinolin-10(10H)-one;

2-[3-(4-fluorophenyl)-3-oxopropyl]-1,2,3,4,4a,5,7,8,9,10a-decahydro-4a,10a-trans-6H-cyclopenta[4,5]pyrrolo[2,3-g]isoquinolin-10(10H)-one;

2-[2-(4-methoxyphenyl)ethyl]-1,2,3,4,4a,5,7,8,9,10a-decahydro-4a,10a-trans-6H-cyclopenta[4,5]pyrrolo[2,3-g]isoquinolin-10(10H)-one;

2-allyl-1,2,3,4,4a,5,7,8,9,10a-decahydro-4a,10a-trans-6H-cyclopenta[4,5]pyrrolo[2,3-g]isoquinolin-10(10H)-one;

2-cyclopropylmethyl-1,2,3,4,4a,5,7,8,9,10a-decahydro-4a,10a-trans-6H-cyclopenta[4,5]pyrrolo[2,3-g]isoquinolin-10(10H)-one;

2-propargyl-1,2,3,4,4a,5,7,8,9,10a-decahydro-4a,10a-trans-6H-cyclopenta[4,5]pyrrolo[2,3-g]isoquinolin-10(10H)-one;

2-[2-(2-thienyl)ethyl]-1,2,3,4,4a,5,7,8,9,10a-decahydro-4a,10a-trans-6H-cyclopenta[4,5]pyrrolo[2,3-g]isoquinolin-10(10H)-one;

2-[2-(2-furyl)ethyl]-1,2,3,4,4a,5,7,8,9,10a-decahydro-4a,10a-trans-6H-cyclopenta[4,5]pyrrolo[2,3-g]isoquinolin-10(10H)-one;

2-[2-(2,3-dihydro-2-oxo-1H-benzimidazol-1-yl)ethyl]-1,2,3,4,4a,5,7,8,9,10a-decahydro-4a,10a-trans-6H-cyclopenta[4,5]pyrrolo[2,3-g]isoquinolin-10(10H)-one;

2-[2-(benzyloxy)ethyl]-1,2,3,4,4a,5,7,8,9,10a-decahydro-4a,10a-trans-6H-cyclopenta[4,5]pyrrolo[2,3-g]isoquinolin-10(10H)-one;

2-(3-phenyl-2-propenyl)-1,2,3,4,4a,5,7,8,9,10a-decahydro-4a,10a-trans-6H-cyclopenta[4,5]pyrrolo[2,3-g]isoquinolin-10(10H)-one;

2-[2-(4-fluorobenzamido)ethyl]-1,2,3,4,4a,5,7,8,9,10a-decahydro-4a,10a-trans-6H-cyclopenta[4,5]pyrrolo[2,3-g]isoquinolin-10(10H)-one;

2-[2-(ethenyloxy)ethyl]-1,2,3,4,4a,5,7,8,9,10a-decahydro-4a,10a-trans-6H-cyclopenta[4,5]pyrrolo[2,3-g]isoquinolin-10(10H)-one;

2-benzyl-1,2,3,4,4a,5,7,8,9,10a-decahydro-4a,10a-trans-6H-cyclopenta[4,5]pyrrolo[2,3-g]isoquinolin-10(10H)-one;

1,2,3,4,4a,5,7,8,9,10a-decahydro-4a,10a-trans-6H-cyclopenta[4,5]pyrrolo[2,3-g]isoquinolin-10(10H)-one;

6-benzoyl-2-methyl-1,2,3,4,4a,5,7,8,9,10a-decahydro-4a,10a-trans-6H-cyclopenta[4,5]pyrrolo[2,3-g]isoquinolin-10(10H)-one;

2,6-dimethyl-1,2,3,4,4a,5,7,8,9,10a-decahydro-4a,10a-trans-6H-cyclopenta[4,5]pyrrolo[2,3-g]isoquinolin-10(10H)-one;

6-benzyl-2-methyl-1,2,3,4,4a,5,7,8,9,10a-decahydro-4a,10a-trans-6H-cyclopenta[4,5]pyrrolo[2,3-g]isoquinolin-10(10H)-one;

6-methyl-2-[4-(4-fluorophenyl)-4-oxobutyl]-1,2,3,4,4a,5,7,8,9,10a-decahydro-4a,10a-trans-6H-cyclopenta[4,5]pyrrolo[2,3-g]isoquinolin-10(10H)-one;

1,2,3,4,4a,5,7,8,9,10a-decahydro-4a,10a-trans-6H-cyclopenta[4,5]pyrrolo[2,3-g]isoquinolin-10(10H)-thione;

2-(2-hydroxy-3,3-dimethylbutyl)-1,2,3,4,4a,5,7,8,9,10a-decahydro-4a,10a-trans-6H-cyclopenta[4,5]pyrrolo[2,3-g]isoquinolin-10(10H)-thione;

2-(2-phenylethyl)-1,2,3,4,4a,5,7,8,9,10a-decahydro-4a,10a-trans-6H-cyclopenta[4,5]pyrrolo[2,3-g]isoquinolin-10(10H)-thione; and 2-[4-(4-fluorophenyl)-4-oxobutyl]-1,2,3,4,4a,5,7,8,9,10a-decahydro-4a,10a-trans-6H-cyclopenta[4,5]pyrrolo[2,3-g]isoquinolin-10(10H)-thione.

Exemplary of the compounds of formula A wherein n is 4, i.e., compounds of the formula

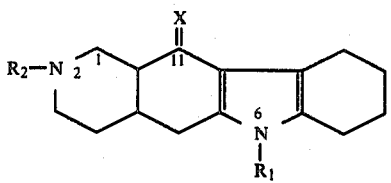

A-2 wherein $R_1$, $R_2$ and X are as previously described, are:

2-(2-hydroxy-3,3-dimethylbutyl)-2,3,4,4a,5,7,8,9,10,11a-decahydro-4a,11a-trans-1H,6H-cyclohexa[4,5]pyrrolo[2,3-g]isoquinolin-11(11H)-one;

2-(2-ethoxyethyl)-2,3,4,4a,5,7,8,9,10,11a-decahydro-4a,11a-trans-1H,6H-cyclohexa[4,5]pyrrolo[2,3-g]isoquinolin-11(11H)-one;

2-cyclobutylmethyl-2,3,4,4a,5,7,8,9,10,11a-decahydro-4a,11a-trans-1H,6H-cyclohexa[4,5]pyrrolo[2,3-g]isoquinolin-11(11H)-one;

2-[2-(2-thienyl)ethyl]-2,3,4,4a,5,7,8,9,10,11a-decahydro-4a,11a-trans-1H,6H-cyclohexa[4,5]pyrrolo[2,3-g]isoquinolin-11(11H)-one;

2-[2-(2-furyl)ethyl]-2,3,4,4a,5,7,8,9,10,11a-decahydro-4a,11a-trans-1H,6H-cyclohexa[4,5]pyrrolo[2,3-g]isoquinolin-11(11H)-one;

2-[3-(4-fluorophenyl)-3-oxopropyl]-2,3,4,4a,5,7,8,9,10,11a-decahydro-4a,11a-trans-1H,6H-cyclohexa[4,5]pyrrolo[2,3-g]isoquinolin-11(11H)-one;

2-(2-propenyl)-2,3,4,4a,5,7,8,9,10,11a-decahydro-4a,11a-trans-1H,6H-cyclohexa[4,5]pyrrolo[2,3-g]isoquinolin-11(11H)-one;

2-(3-phenoxypropyl)-2,3,4,4a,5,7,8,9,10,11a-decahydro-4a,11a-trans-1H,6H-cyclohexa[4,5]pyrrolo[2,3-g]isoquinolin-11(11H)-one;

2-[3-(2,3-dihydro-2-oxo-1H-benzimidazol-1-yl)propyl]-2,3,4,4a,5,7,8,9,10,11a-decahydro-4a,11a-trans-1H,6H-cyclohexa[4,5]pyrrolo[2,3-g]isoquinolin-11(11H)-one;

2-benzyl-2,3,4,4a,5,7,8,9,10,11a-decahydro-4a,11a-trans-1H,6H-cyclohexa[4,5]pyrrolo[2,3-g]isoquinolin-11(11H)-one;

2,3,4,4a,5,7,8,9,10,11a-decahydro-4a,11a-trans-1H,6H-cyclohexa[4,5]pyrrolo[2,3-g]isoquinolin-11(11H)-one;

2,6-dimethyl-2,3,4,4a,5,7,8,9,10,11a-decahydro-4a,11a-trans-1H,6H-cyclohexa[4,5]pyrrolo[2,3-g]isoquinolin-11(11H)-one;

6-benzoyl-2-[4-(4-fluorophenyl)-4-oxobutyl]-2,3,4,4a,5,7,8,9,10,11a-decahydro-4a,11a-trans-1H,6H-cyclohexa[4,5]pyrrolo[2,3-g]isoquinolin-11(11H)-one;

2-(2-phenylethyl)-2,3,4,4a,5,7,8,9,10,11a-decahydro-4a,11a-trans-1H,6H-cyclohexa[4,5]pyrrolo[2,3-g]isoquinolin-11(11H)-thione;

2,3,4,4a,5,7,8,9,10,11a-decahydro-4a,11a-trans-1H,6H-cyclohexa[4,5]pyrrolo[2,3-g]isoquinolin-11(11H)-thione; and 2-[4-(4-fluorophenyl)-4-oxobutyl]-2,3,4,4a,5,7,8,9,10,11a-decahydro-4a,11a-trans-1H,6H-cyclohexa[4,5]pyrrolo[2,3-g]isoquinolin-11(11H)-thione.

In the compounds of formula A-2 wherein X is O, an alternative nomenclature may be employed. Thus, for example, 2-methyl-2,3,4,4a,5,7,8,9,10,11a-decahydro-4a,11a-trans-1H,6H-cyclohexa[4,5]pyrrolo[2,3-g]isoquinolin-11(11H)-one; and 2-methyl-2,3,4,4a,5,7,9,10,11a-decahydro-4a,11a-trans-pyrido[4,3-b]carbazol-11(1H,6H)-one are one and the same compound.

Exemplary of the compounds of formula A wherein n is 5, i.e., compounds of the formula

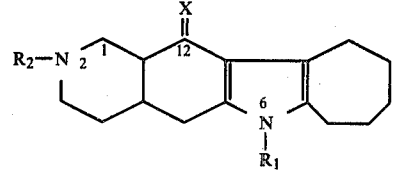

A-3 wherein $R_1$, $R_2$ and X are as previously described, are:

2-methyl-1,2,3,4,4a,5,7,8,9,10,11,12a-dodecahydro-4a,12a-trans-6H-cyclohepta[4,5]pyrrolo[2,3-g]isoquinolin-12(12H)-one;

2-[4-(4-fluorophenyl)-4-oxobutyl]-1,2,3,4,4a,5,7,8,9,10,11,12a-dodecahydro-4a,12a-trans-6H-cyclohepta[4,5]pyrrolo[2,3-g]isoquinolin-12(12H)-one;

2-(3-phenoxypropyl)-1,2,3,4,4a,5,7,8,9,10,11,12a-dodecahydro-4a,12a-trans-6H-cyclohepta[4,5]pyrrolo[2,3-g]isoquinolin-12(H)-one;

2-(2-phenylethyl)-1,2,3,4,4a,5,7,8,9,10,11,12a-dodecahydro-4a,12a-trans-6H-cyclohepta[4,5]pyrrolo[2,3-g]isoquinolin-12(12H)-one;

2-[4-(4-fluorophenyl)-4-oxobutyl]-1,2,3,4,4a,5,7,8,9,10,11,12a-dodecahydro-4a,12a-trans-6H-cyclohepta[4,5]pyrrolo[2,3-g]isoquinolin-12(12H)-thione;

2-(3-phenoxypropyl)-1,2,3,4,4a,5,7,8,9,10,11,12a-dodecahydro-4a,12a-trans-6H-cyclohepta[4,5]pyrrolo[2,3-g]isoquinolin-12(12H)-thione; and 2-(2-phenylethyl)-1,2,3,4,4a,5,7,8,9,10,11,12a-dodecahydro-4a,12a-trans-6H-cyclohepta[4,5]pyrrolo[2,3-g]isoquinolin-12(12H)-thione.

Exemplary of the compounds of formula A wherein n is 6, i.e., compounds of the formula

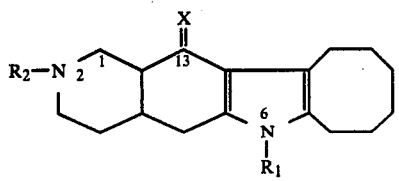
A-4 wherein R₁, R₂ and X are as previously described, are:

2-[4-(4-fluorophenyl)-4-oxobutyl]-2,3,4,4a,5,7,8,9,10,11,12,13a-dodecahydro-4a,13a-trans-1H,6H-cycloocta[4,5]pyrrolo[2,3-g]isoquinolin-13(13H)-one;

2-(2-phenylethyl)-2,3,4,4a,5,7,8,9,10,11,12,13a-dodecahydro-4a,13a-trans-1H,6H-cycloocta[4,5]pyrrolo[2,3-g]isoquinolin-13(13H)-one;

2-(2-hydroxy-3,3-dimethylpropyl)-2,3,4,4a,5,7,8,9,10,11,12,13a-dodecahydro-4a,13a-trans-1H,6H-cycloocta[4,5]pyrrolo[2,3-g]isoquinolin-13(13H)-one;

2-methyl-2,3,4,4a,5,7,8,9,10,11,12,13a-dodecahydro-4a,13a-trans-1H,6H-cycloocta[4,5]pyrrolo[2,3-g]isoquinolin-13(13H)-one;

2-(3-phenoxypropyl)-2,3,4,4a,5,7,8,9,10,11,12,13a-dodecahydro-4a,13a-trans-1H,6H-cycloocta[4,5]pyrrolo[2,3-g]isoquinolin-13(13H)-one;

2-[4-(4-fluorophenyl)-4-oxobutyl]-2,3,4,4a,5,7,8,9,10,11,12,13a-dodecahydro-4a,13a-trans-1H,6H-cycloocta[4,5]pyrrolo[2,3-a]isoquinolin-13H(13H)-thione;

2-(2-phenylethyl)-2,3,4,4a,5,7,8,9,10,11,12,13a-dodecahydro-4a,13a-trans-1H,6H-cycloocta[4,5]pyrrolo[2,3-g]isoquinolin-13(13H)-thione;

2-(2-ethoxyethyl)-2,3,4,4a,5,7,8,9,10,11,12,13a-dodecahydro-4a,13a-trans-1H,6H-cycloocta[4,5]pyrrolo[2,3-g]isoquinolin-13(13H)-thione; and 2-(3-phenoxypropyl)-2,3,4,4a,5,7,8,9,10,11,12,13a-dodecahydro-4a,13a-trans-1H,6H-cycloocta[4,5]pyrrolo[2,3-g]isoquinolin-13(13H)-thione.

The compounds of the invention wherein n is 3 can exist as the 4a,10a-trans or 4a,10a-cis isomers or mixtures thereof; the 4a,10-trans isomers are preferred.

The compounds of the invention wherein n is 4 can exist as the 4a,11a-trans or 4a,11a-cis isomers or mixtures thereof; the 4a,11a-trans isomers are preferred.

The compounds of the invention wherein n is 5 can exist as the 4a,12a-trans or 4a,12a-cis isomers or mixtures thereof; the 4a,12a-trans isomers are preferred.

The compounds of the invention wherein n is 6 can exist as the 4a,13a-trans or 4a,13a-cis isomers or mixtures thereof; the 4a,13a-trans isomers are preferred.

More specifically, the compounds of formula A wherein X is O are characterized by the formula

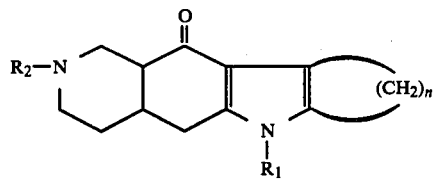
I wherein n, R₁ and R₂ are as hereinbefore described, and can be prepared as set forth in Schemes I, II, III and IV and further described.

FORMULA SCHEME I

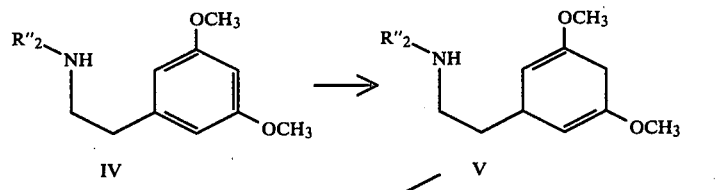

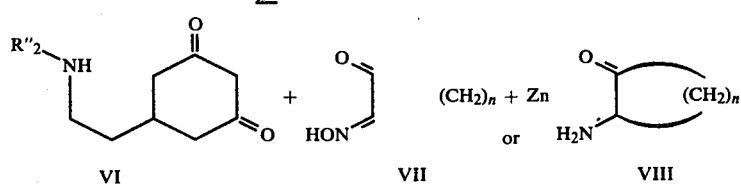

-continued
FORMULA SCHEME I

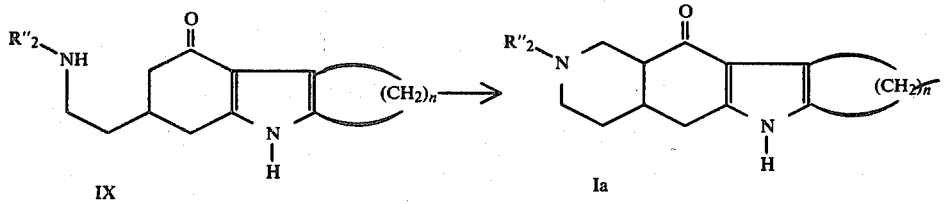

wherein n is as previously described, and R₂" is alkyl, alkoxyalkyl, or cycloalkyl-alkyl.

In accordance with Formula Scheme I, compounds of formula Ia are prepared from known compounds of formula IV wherein R₂" is alkyl, alkoxyalkyl or cycloalkylalkyl. Birch reduction of the amine of formula IV with lithium in ammonia containing t-butanol yields the dihydroamine of formula V. Other modifications of the Birch reduction may also be employed. Thus, the amine of formula IV may be reacted with an alkali metal, such as sodium, lithium, potassium or cesium, in ammonia or an amine such as methylamine or ethylamine in the presence of a lower alkanol such as ethanol, butanol, or t-butanol. The reaction is generally carried out at the boiling point of the solvent or below, for example, from $-78°$ to $15°$ C. If ammonia is used, the reaction is run at reflux. Optionally, cosolvents such as diethyl ether or tetrahydrofuran may be added.

The hydrolysis of the dihydroamine of formula V is readily accomplished by the usual methods for hydrolysis of enol ethers, for example, with aqueous acid. Exemplary of acids which may be used are hydrochloric acid, hydrobromic acid, formic acid, acetic acid, p-toluenesulfonic acid and perchloric acid. These may be used in aqueous solutions or mixed solvents. Tetrahydrofuran, benzene, diethyl ether, acetone, toluene, dioxane or acetonitrile are exemplary of the solvents which may be employed. For example, hydrolysis of the dihydroamine of formula V wherein R₂" is methyl in 2 N hydrochloric acid at room temperature or above or in aqueous acetic acid at between 40° and reflux leads to the diketone of formula VI, wherein R₂" is methyl.

The diketone of formula VI is condensed in a Knorr condensation to give the methylaminoethyl ketone of formula IX. The Knorr condensation is a well-known method for the preparation of pyrroles and the process may be used in any of the well-known modifications [see, for exemplary conditions, J. M. Patterson, Synthesis, 281 (1976) and references therein]. For example, the reaction of an isonitrosoketone of formula VII in the presence of a reducing agent, for example with zinc in aqueous acetic acid or hydrochloric acid, is thought to proceed via the aminocarbonyl compound of formula VIII which then condenses with the diketone of formula VI to give the product methylaminoethyl ketone of formula IX. Alternatively, the condensation can be carried out with an aminocarbonyl compound of formula VIII or precursor thereof, such as an aminoketone hydrochloride salt, or a ketal derivative of an aminoketone. The use of a precursor of the aminoketone is preferred, since such substances are prone to self-condensation. They may best be utilized in situ where the aminocabonyl component is liberated in the presence of the diketone of formula VI. The aminocarbonyl component immediately reacts to form the compound of formula IX. It is not necessary to isolate the diketone of formula VI prior to carrying out the Knorr condensation since the reaction conditions employed are sufficient to hydrolyze the dihydroamine of formula V to the diketone of formula VI. The Knorr condensation is best carried out at a pH of from about pH 2 to pH 6. Much above pH 6, there is a considerable loss in yield due to the formation of self-condensation products of the aminocarbonyl compound of formula VIII.

Preferably, an isonitrosoketone of formula VII and zinc dust in aqueous acetic acid is condensed with a diketone of formula VI wherein R₂" is methyl to give the product methylaminoethyl ketone of formula IX wherein R₂" is methyl.

The Knorr condensation is preferably carried out at a temperature range of from about room temperature to reflux. The isonitrosoketones of formula VII are known compounds or can readily be prepared by nitrosation of the corresponding β-ketoester, for example, with sodium nitrite. [see, for example, T. A. Geissman and M. J. Schlatter, *J. Org. Chem.*, 11, 771 (1946)].

Exemplary of isonitrosoketones of formula VIII which can be used in the Knorr condensation are:
2-isonitrosocyclopentanone;
2-isonitrosocyclohexanone;
2-isonitrosocycloheptanone; and
2-isonitrosocyclooctanone.

Exemplary of aminocarbonyl precursor compounds of formula VIII which can be used in the Knorr condensation are:
2-aminocyclohexanone, hydrochloride;
2-aminocyclopentanone, hydrochloride;
2-aminocycloheptanone, hydrochloride; and
2-aminocyclooctanone, hydrochloride.

Said compounds are known or may be prepared by reduction of the corresponding isonitrosoketone, for example, by catalytic hydrogenation in the presence of hydrogen chloride.

The amine of the formula IX is converted to the compound of the formula Ia via an intramolecular Mannich reaction. The Mannich reaction is usually performed starting with a ketone and a dialkylamine salt, for example, dimethylamine hydrochloride and formaldehyde (for example, as an aqueous solution, as paraformaldehyde or as trioxane) in an alcoholic solvent such as ethanol, at the reflux temperature of the reaction mixture. In the modification herein described, an acid addition salt of the methylaminoethyl-ketone of formula IX is reacted with formaldehyde, added in the form of paraformaldehyde, trioxane, or as aqueous formaldehyde in a solvent. For example, a high boiling hydroxylic solvent, such as amyl alcohol, octanol, ethylene glycol or diethylene glycol monoethyl ether; a high boiling polar aprotic solvent, such as dimethylformamide, N-methylpyrrolidinone or diethylene glycol dimethyl ether; a lower boiling polar solvent, such as ethanol, butanol or 2-propanol, under pressure; or a lower boiling aprotic solvent under pressure, such as dioxane or tetrahydrofuran, may be used at a temperature in the range of from about 135° C. to about 200° C. to yield the cycloalka[4,5]pyrrolo[2,3-g]isoquinolines of formula Ia. The reaction, especially when run at temperatures below 150° C. leads to a mixture of cis and trans isomers, i.e., for example, when $R_2''$ is methyl, compounds of the formulas

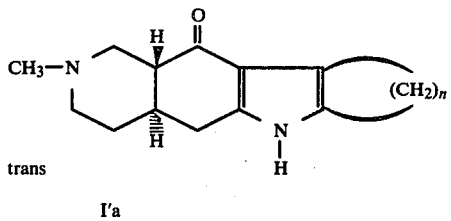

trans

I′a

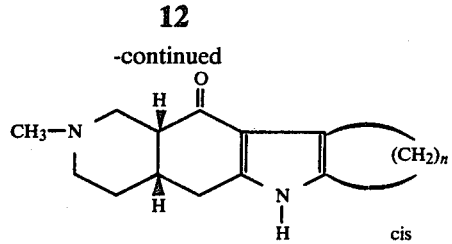

-continued

I″a cis

Longer heating of the reaction mixture or separate heating of the isomeric mixture of hydrochloride salts of formulas I′a and I″a, for example, in ethylene glycol at reflux for 2 hours can be used to equilibrate the cis and trans isomers to a final ratio which comprises predomonantly the trans isomer, which is readily isolated by crystallization or by chromatographic separation.

For example, when the hydrochloride salt of the amine of formula IX wherein $R_2''$ is methyl is reacted with paraformaldehyde in butanol at 180° for 2 hours, the product is isolated as the trans isomer I′a.

FORMULA SCHEME II

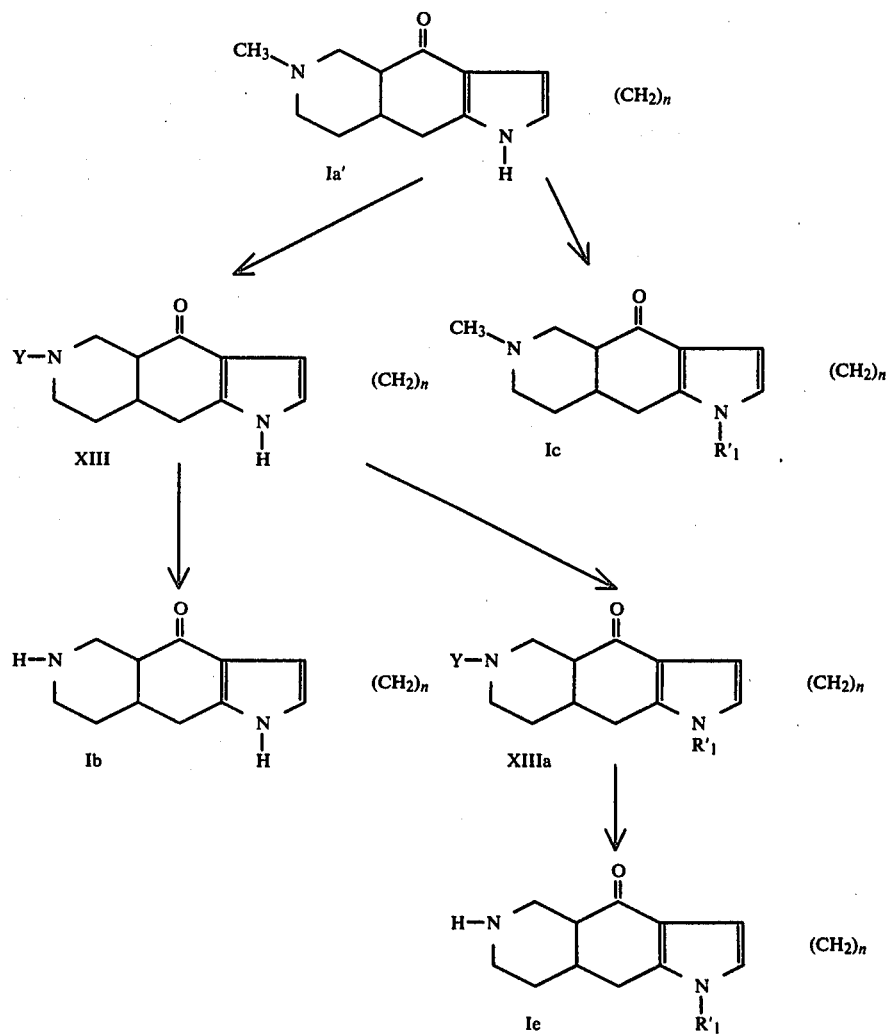

wherein n is as previously described, Y is a urethane group, and $R_1'$ is alkyl, acyl or aralkyl.

In accordance with Formula Scheme II, compounds of formula Ic are prepared by alkylation or acylation of the pyrrole nitrogen of a compound of formula Ia' and other N-2-alkyl derivatives by formation of the pyrrole anion with strong base, for example, sodium amide, potassium hydride, sodium methylsulfinyl carbanion, potassium t-butoxide, or butyllithium, or with an alkali metal, followed by quenching with an alkyl or acyl halide in a solvent such as tetrahydrofuran, dioxane, ethyl ether, dimethylformamide or dimethylsulfoxide. For example, treatment of a compound of formula Ia', wherein n is 3 with potassium t-butoxide in tetrahydrofuran followed by quenching with methyl iodide affords the 6-methyl derivative, i.e., a compound of formula Ic wherein n is 3 and $R_1'$ is methyl. Similarly, reaction of a compound of formula Ia', wherein n is 4 with butyllithium in tetrahydrofuran at $-30°$ followed by quenching with benzoyl chloride affords the 6-benzoyl derivative, i.e., a compound of formula Ic wherein $R_1'$ is benzoyl and n is 4. Similarly, reaction of a compound of formula Ia', wherein n is 3, with sodium methylsulfinyl carbanion in dimethylsulfoxide followed by quenching with benzyl chloride affords the 6-benzyl derivative, i.e., a compound of formula Ic wherein $R_1'$ is benzyl and n is 3.

N-Demethylation of the compound of formula Ia' can be accomplished by standard N-dealkylation procedures, such as the von Braun method [H. A. Hageman, Org. Reactions, 7, 198 (1953)], or via acid or base hydrolysis of a urethane derivative such as those listed in K. C. Rice [J. Org. Chem., 40, 1850 (1975)]. One procedure for the dealkylation of the compound of formula Ia' is via the urethane of formula XIII, wherein Y is

and acid hydrolysis, to give the secondary amine of formula Ib. For example, a compound of formula Ia', wherein n is 4, when refluxed in dioxane with excess ethyl chloroformate and potassium bicarbonate for 6 hours gives a compound of formula XIII, wherein Y is

and wherein n is 4. Hydrolysis of the foregoing compound with 30% aqueous sodium hydroxide in ethanol-dioxane at reflux for 24 hours gives the compound of formula Ib, wherein n is 4.

Urethane derivatives may also be employed as starting materials for the preparation of pyrrole-ring substituted derivatives of formula Ie by alkylation or acylation at the pyrrole nitrogen, followed by cleavage of the urethane. The alkylation or acylation is carried out following the procedures given for the preparation of compounds of formula Ic, and the urethane derivatives and procedures for their cleavage are given, as mentioned above, in K. C. Rice (ibid). For example, in accordance with Formula Scheme II, treatment of the ethoxycarbonyl urethane of formula XIII, wherein Y is

and n is 4 with sodium methylsulfinyl carbanion in dimethylsulfoxide, followed by treatment with benzyl chloride, affords the compound of formula XIIIa, wherein Y is

and n is 4 and $R_1'$ is benzyl. Hydrolysis with sodium hydroxide affords the 6-benzyl derivative, i.e., a compound of the formula Ie wherein $R_1'$ is benzyl and n is 4. In cases where $R_1'$ is an acyl group which could be hydrolyzed under vigorous alkaline or strongly acidic conditions, a urethane group such as 2,2,2-trichloroethoxycarbonyl, which may be cleaved under mild conditions with zinc in aqueous acetic acid, may be employed to give compounds of formula Ie wherein $R_1'$ is acyl.

FORMULA SCHEME III

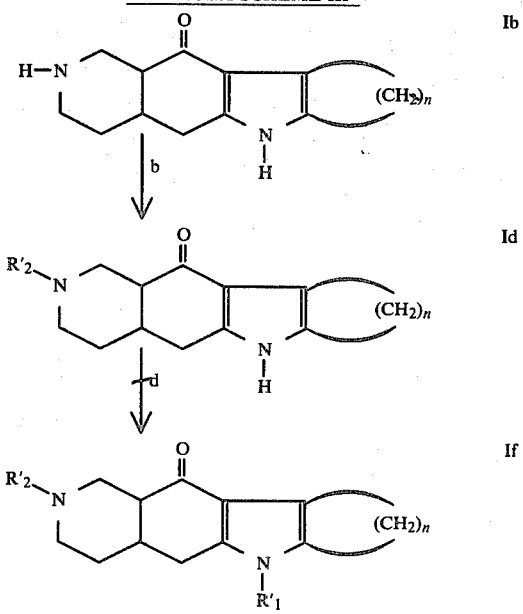

wherein n is as previously described, and $R_1'$ is alkyl, acyl, or aralkyl, and $R_2'$ is alkyl, hydroxyalkyl, arylhydroxyalkyl, alkoxyalkyl, acyloxyalkyl, acylalkyl, aralkyl, alkenyl, cycloalkyl-alkyl, thienyl-alkyl, alkynyl, furyl-alkyl, arylcarboxamidoalkyl, aralkenyl, alkenyloxyalkyl, aryloxyalkyl, aralkyloxyalkyl, or aryl-N-imidazolonylalkyl.

In accordance with Formula Scheme III, the comounds of formulas Id and If are prepared from the secondary amine of formula Ib, the starting material for the preparation of numerous derivatives encompassed by formula I, by substitution at the basic amine nitrogen (N-2) and/or the pyrrole nitrogen (N-6). For example, treatment of a compound of formula Ib with an alkyl halide, such as ethyl bromide, an alkenyl halide, such as allyl bromide, a cycloalkyl-alkyl halide, such as chloromethylcyclopropane, an aralkyl halide, such as benzyl bromide, or an acylalkyl halide such as γ-chloro-p- fluorobutyrophenone, in the presence of a base, for example, potassium carbonate, in acetone, 2-propanone or dimethylformamide, yields the correspondingly substituted compound of formula Id, that is, wherein R₂' is alkyl, alkenyl, cycloalkyl-alkyl, aralkyl, or acylalkyl, respectively. With reactive halides, the reaction may be run at room temperature; with less reactive halides, reflux temperatures are used, and in some cases, the reaction rate can be enhanced by the addition of an iodide salt, such as lithium iodide, to the reaction mixture.

Reaction of a compound of formula Ib with epoxyalkanes gives the hydroxyalkyl substituted compound of formula Id. Treatment with a substituted epoxyalkane gives the 2-substituted-2-hydroxyalkyl analogs of a compound of formula Id, for example, reaction of a compound of formula Ib with styrene oxide gives a compound of formula Id, wherein R₂' is 2-phenyl-2-hydroxyethyl. The reaction is usually carried out in the presence of an alcoholic solvent such as methanol, at from about room temperature to the reflux temperature of the mixture. The epoxyalkanes are either commercially available or are prepared by epoxidation of the corresponding olefins, or by methylenation of a ketone with a sulfonium methylide or sulfoxonium methylide reagent, for example, dimethylsulfonium methylide. Thus, for example, treatment of benzaldehyde with dimethylsulfonium methylide gives styrene oxide.

In some cases, where R₂' in the compound of formula Id does not contain functional groups capable of undergoing alkylation or acylation, the procedures outlined in Formula Scheme II for the preparation of compounds of formula Ic can be used directly to prepare N-6 substituted analogs of formula If as depicted in Formula Scheme III. Alkylations can occur in compounds wherein R₂' is hydroxyalkyl or arylhydroxyalkyl. The hydroxyl groups therein must be protected with a base-stable protecting group, such as tetrahydropyranyl. After N-6 alkylation, the protecting group is removed by acid hydrolysis.

Alternatively, compounds of formula Id, wherein R₂' is hydroxyalkyl or aryl hydroxyalkyl may be prepared by reduction of the corresponding compounds of formula Id wherein R₂' is acylalkyl. More particularly, the foregoing reduction may be carried out, for example, with an alkali metal borohydride reducing agent, such as sodium borohydride or lithium borohydride at, for example, room temperature in a solvent, for example, an alkanol, such as ethanol, or the like.

In the reactions described in Formula Schemes I, II and III, both the trans isomers of the formula

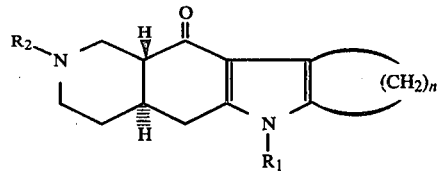

I' wherein n, R₁ and R₂ are as previously described, and cis isomers of the formula

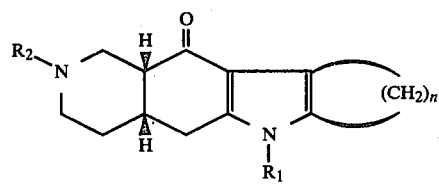

I'' wherein n, R₁ and R₂ are as previously described, of the compounds of formula I may be formed, with the trans isomer predominating. The pure trans isomer may be separated by chromatography or crystallization. In addition, the mixture may be isomerized as described for the isomerization of the trans and cis isomers of the oxo compound of formula I'a and I''a, or by base-catalyzed equilibration, for example, with sodium hydroxide in ethanol.

When the substituent groups R₁ and R₂ in compounds of the formula I contain additional asymmetric centers, a mixture of diasteriomers may be obtained. For example, the number of isomers possible is $2^n$ wherein n is the total number of asymmetric centers in the compound. Preferred are the enantiomers and/or diastereomers of compound of the formula I', hereinbefore described.

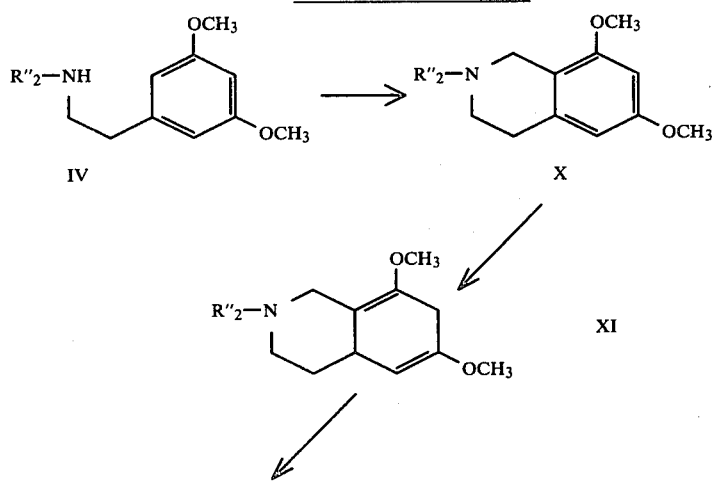

FORMULA SCHEME IV

-continued

FORMULA SCHEME IV

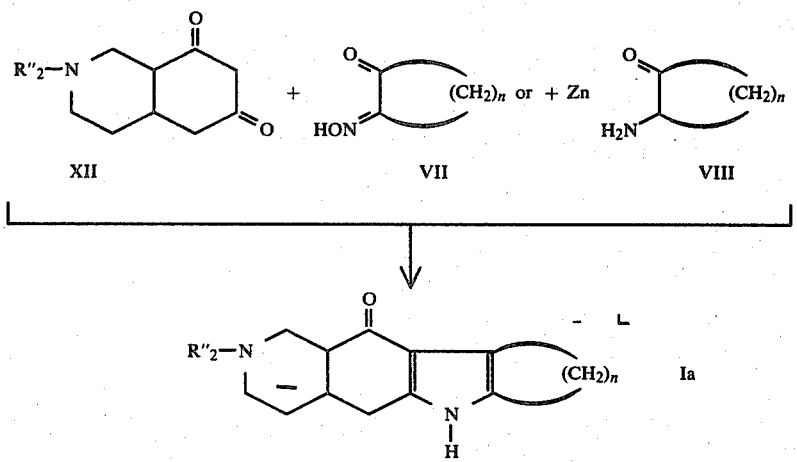

wherein n is as previously described, and R₂″ is alkyl, alkoxyalkyl, or cycloalkyl-alkyl.

An alternative synthesis of the compounds of formula Ia is described in Formula Scheme IV, in which the isoquinoline ring is formed prior to the formation of the pyrrole ring. In accordance with Formula Scheme IV, the (3,5-dimethoxyphenyl)-ethylamine of formula IV is refluxed with aqueous formaldehyde to give the tetrahydroisoquinoline of formula X. Birch reduction of the tetrahydroisoquinoline of formula X with lithium in liquid ammonia containing t-butanol under conditions substantially the same as described for the Birch reduction of the compound of formula IV yields the hexahydroisoquinoline of formula XI. Hydrolysis of crude hexahydroisoquinoline of formula XI under conditions substantially the same as described for the hydrolysis of the dihydroamine of the formula V yields the diketone of formula XII. The compound of formula XII is reacted in a Knorr condensation, as described in the preparation of methylaminoethyl ketone of formula IX with the isonitrosoketone of formula VII or with the aminocarbonyl compound of formula VIII to give the cycloalka[4,5]pyrroloisoquinoline of formula Ia. Preferred is the sequence of reactions in accordance with Formula Scheme IV starting with the amine of formula IV, wherein R₂″ is methyl-cycloalka[4,5]pyrroloisoquinoline of formula Ia, as a mixture containing the trans isomer I′a and the cis isomer of formula I″a.

The same procedures for isomerization of the mixture of cycloalka[4,5]pyrroloisoquinolines of formulas I′ and I″ as described previously may be employed to yield mainly the trans isomer of formula I′a.

The compounds of formula A wherein X is S are characterized by the formula

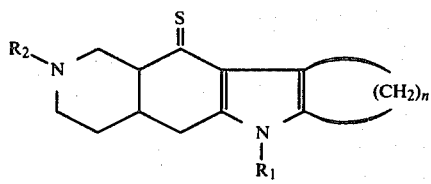

wherein n, R₁ and R₂ are as hereinbefore described, and can be prepared as set forth in Formula Schemes V and VI, and further described hereinafter.

FORMULA SCHEME V

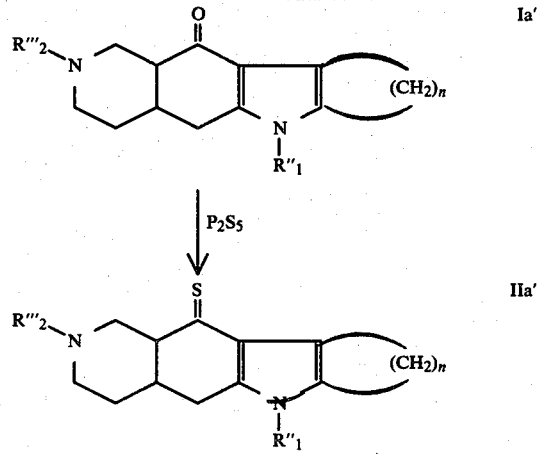

wherein n is as previously described; R₁‴ is hydrogen, alkyl, or aralkyl; and R₂‴ is hydrogen, alkyl, alkoxyalkyl, aralkyl, alkenyl, aryloxyalkyl, thienylalkyl, furyl-alkyl, alkynyl, aralkenyl, alkenyloxyalkyl, aralkyloxyalkyl or cycloalkyl-alkyl.

In accordance with Formula Scheme V, compounds of formula IIa′ are prepared by heating compounds of formula Ia′ with phosphorus pentasulfide in an inert organic solvent. Preferred solvents are tetrahydrofuran, benzene, toluene or dioxane, and the reaction is generally run at the reflux temperature.

Additional compounds of formula II are prepared as described in Formula Scheme VI. In accordance with Formula Scheme VI, a compound of formula IIb is reacted to give a compound of formula IId following the procedures detailed in Formula Scheme III for the preparation of the corresponding oxo compounds of Formula Ib.

FORMULA SCHEME VI

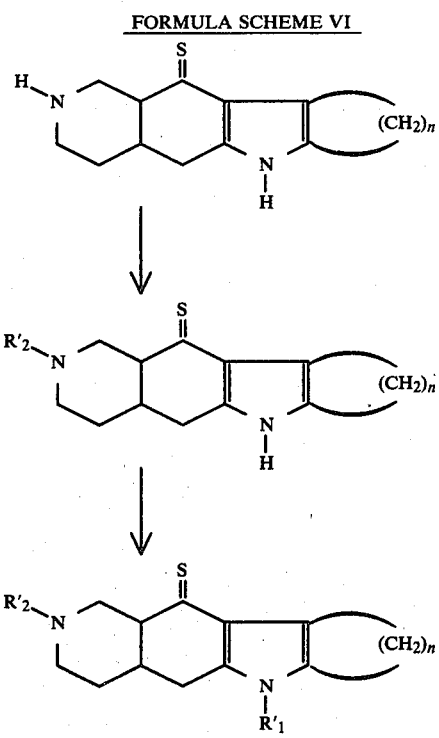

wherein n, R₁' and R₂' are as previously described.

Similarly, a compound of formula IId is reacted to give a compound of formula IIf following the procedures outlined in Scheme III for the preparation of the corresponding oxo compounds of formula If.

Additional compounds of formula II are prepared following the procedures detailed in Formula Scheme II for the preparation of corresponding oxo compounds of formula Ie.

In these reactions, both the trans isomers of the formula

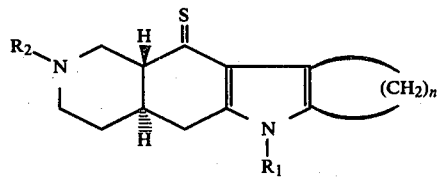

wherein n, R₁ and R₂ are as previously described, and cis isomers of the formula

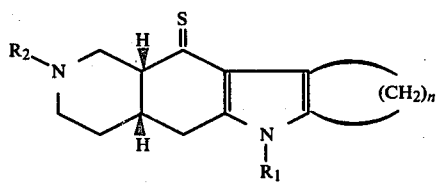

wherein n, R₁ and R₂ are as previously described, of the compounds of formula II may be formed, with the trans isomer predominating. The pure trans isomer may be separated by chromatography or crystallization. In addition, the mixture may be isomerized as described for the isomerization of the trans and cis isomers of the oxo compound of formula I'a and I"a.

As described above for compounds of formula I, when substituent groups $R_1$ and $R_2$ in compounds of formula II contain additional asymmetric centers, a mixture of diastereomers may be obtained. Preferred are the enantiomers and/or diastereomers of compounds of the formula II', hereinbefore described.

The compounds of formula A form acid addition salts with inorganic or organic acids. Thus, they form pharmaceutically acceptable acid addition salts with both pharmaceutically acceptable organic and inorganic acids, for example, with hydrohalic acid, such as, hydrochloric acid, hydrobromic acid, hydroiodic acid, other mineral acid salts, such as sulfuric acid, nitric acid, phosphoric acid, or the like, alkyl- and mono-aryl sulfonic acids, such as ethanesulfonic acid, toluenesulfonic acid, benzenesulfonic acid, or the like, other organic acids such as acetic acid, tartaric acid, maleic acid, citric acid, benzoic acid, salicylic acid, ascorbic acid, and the like. Non-pharmaceutically acceptable acid addition salts of compounds of formula A can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically accetpable acid addition salt and then reacting the so-obtained free base with a reagent yielding a pharmaceutically acceptable acid addition salt. The acid addition salts may also form hydrates.

The compounds of formula A and their pharmaceutically acceptable acid addition salts exhibit neuroleptic activity. Accordingly, the compounds of formula A are useful as antipsychotic agents, for instance, in the treatment of schizophrenia. The activity of the compounds of formula A which makes them useful as antipsychotic agents can be demonstrated in warm-blooded animals, in accordance with known procedures.

For example, by one procedure, trained rats are placed in experimental chambers equipped with a response lever, a steel grid floor for delivery of electric shock and a loudspeaker for presentation of auditory stimuli. Each trial consists of a fifteen-second warning tone, (conditioned stimulus), continuing for an additional fifteen seconds accompanied by electric shock (unconditioned stimulus; 1.0 mA, 350 V.A.C.). The rats can terminate a trial at any point by depression of the response lever. A response during the initial fifteen-second warning tone ends the trial before shock delivery and is considered an avoidance response, while a response occurring during shock delivery is an escape response. Trials are presented every two minutes during a one-hour test session 30 trials per session).

Trained rats maintain a reliable control baseline of avoidance behavior (zero to three avoidance failures per session). Compounds are administered at appropriate pretreatment times to a minimum of three to four rats at each dose level over a range of doses. Rats receive vehicle alone, during control sessions. One control and one experimental session are alternated during each week.

The session is divided into three consecutive twenty minute (ten trial) segments. Response counts are summed over all subjects at a given dose within each segment.

The number of trials in which the rats failed to exhibit an avoidance response (avoidance block; AB) or failed to exhibit an escape response (escape block; EB) is determined for the segment displaying the maximum such effect at each dose. This number is expressed as a percentage of the total trials within the segment. The dose calculated to produce a 50% block of avoidance (ABD 50) is obtained from the dose-effect regression line fitted by the Method of Least Squares. The lowest dose which produced a 20% block of escape responding (EBD 20) is read from a graphic dose-effect plot. In obtaining these values, percent effect is plotted against the log dose.

Antipsychotic agents can be distinguished from other types of drugs, which affect the behavior of rats in this procedure, by the larger separation between doses which block avoidance responding and doses which block escape responding. The clinical potency of antipsychotic drugs with known therapeutic uses and properties is significantly and highly correlated with their potency in this procedure. Consequently, the compounds of formula A may be used therapeutically in dosage ranges consistent with their potency in the test procedure.

When 2-methyl-1,2,3,4,4a,5,7,8,9,10a-decahydro-4a,10a-trans-6H-cyclopenta[4,5]-pyrrolo[2,3-g]isoquinolin-10(10H)-one is utilized as the test substance, neuroleptic activity is observed at an $ABD_{50}$ of 0.98 mg/kg p.o.

Similarly, when 2-[4-(4-fluorophenyl)-4-oxobutyl]-1,2,3,4,4a,5,7,8,9,10a-decahydro-4a,10a-trans-6H-cyclopenta[4,5]pyrrolo[2,3-g]isoquinolin-10(10H)-one is utilized as the test substance, neuroleptic activity is observed at an $ABD_{50}$ of 0.15 mg/kg p.o.

Similarly, when 2-[4-(4-fluorophenyl)-4-oxobutyl]-2,3,4,4a,5,7,8,9,10,11a-decahydro-4a,11a-trans-1H,6H-cyclohexa[4,5]pyrrolo[2,3-g]isoquinolin-11(11H)-one is utilized as the test substance, neuroleptic activity is observed at an $ABD_{50}$ of 0.73 mg/kg p.o.

Similarly, when 2-methyl-2,3,4,4a,5,7,8,9,10,11a-decahydro-4a,11a-trans-1H,6H-cyclohexa[4,5]pyrrolo[2,3-g]isoquinolin-11(11H)-one, hydrochloride, 0.75 molar hydrate, which has demonstrated an $LD_{50}$ of, for example, 650 mg/kg p.o in mice, is utilized as the test substance, neuroleptic activity is observed at an $ABD_{50}$ of 5.5 mg/kg p.o.

Similarly, when 2-methyl-2,3,4,4a,5,7,8,9,10,11,12,13a-dodecahydro-4a,13a-trans-1H,6H-cycloocta[4,5]pyrrolo[2,3-g]isoquinolin-13(13H)-one is utilized as the test substance, neuroleptic activity is observed at 8 mg/kg p.o. where the avoidance blockade is 63%.

Similarly, when 2-methyl-1,2,3,4,4a,5,7,8,9,10,11,12a-dodecahydro-4a,12a-trans-6H-cyclohepta[4,5]pyrrolo[2,3-g]isoquinolin-12(12H)-one is utilized as the test substance, neuroleptic activity is observed at 16 mg/kg p.o. where the avoidance blockade is 50%.

The compounds of formula A and their pharmaceutically acceptable acid addition salts have antipsychotic effects which are qualitatively similar to those of haloperidol, and trifluoperazine, known for their therapeutic uses and properties. Thus, the compounds of formula A demonstrate a pattern of activity associated with antipsychotic drugs of known efficacy and safety.

The compounds of formula A and their pharmaceutically acceptable acid addition salts can be used in the form of conventional pharmaceutical preparations. By way of exemplification, suitable oral dosage units comprise or are in the range of from 0.05 to 50 mg., and suitable oral dosage regimens in warm-blooded animals comprise or are in the range of from about 0.001 mg/kg per day to about 10 mg/kg per day. However, for any particular warm-blooded animal, the specific dosage regimen may be variable and should be adjusted according to individual need and the professional judgment of the person administering or supervising the administration of a compound of formula A or a pharmaceutically acceptable acid addition salt thereof. Furthermore, the frequency with which any such dosage form will be administered will vary, depending upon the quantity of active medicament present therein and the needs and requirements of the pharmacological situation.

For the disclosed use, the compounds of formula A and their pharmaceutically acceptable acid addition salts are formulated, using conventional inert pharmaceutical adjuvant materials, into dosage forms which are suitable for oral or parenteral administration. Such dosage forms include tablets, suspensions, solutions, and the like. Furthermore, the compounds of formula A can be embodied into, and administered in the form of, suitable hard or soft capsules. The identity of the inert adjuvant materials which are used in formulating the compounds of formula A and their pharmaceutically acceptable acid addition salts into oral and parenteral dosage forms will be immediately apparent to persons skilled in the art. These adjuvant materials, either inorganic or organic in nature, include, for example, water, gelatin, lactose, starch, magnesium stearate, talc, vegetable oils, gums, polyalkylene glycols, etc. Moreover, preservatives, stabilizers, wetting agents, emulsifying agents, salts for altering osmotic pressure, buffers, or the like, can be incorporated, if desired, into such formulations.

Since the compounds of formula A and their pharmaceutically acceptable acid addition salts possess asymmetric carbon atoms, they are ordinarily obtained as racemic mixtures. If desired, diastereomeric mixtures, when obtained, may be separated. The resolution of individual racemates into the optically active isomers can be carried out by known procedures. Alternatively, optically active isomers can be prepared utilizing, in the processes herein described, corresponding optically active starting materials. Some racemic mixtures can be precipitated as eutectics and can thereafter be separated. Chemical resolution is, however, preferred. By this method, diastereomers are formed from the racemic mixture with an optically active resolving agent, for example, an optically active acid, such as (+)-tartaric acid, (+)-dibenzoyl-D-tartaric acid, (+)-d-10-camphor-sulfonic acid, (−)-3-pinanecarboxylic acid, and the like, to form a diastereomeric salt. The formed diastereomers are separated by fractional crystallization and can be converted to the corresponding optical isomer base. Thus, the invention covers the optically active isomers of the compounds of formula A as well as their racemates.

Furthermore, due to the possible different spatial arrangements of their atoms, it is to be understood that the compounds of this invention may be obtained in more than one possible geometric isomeric form. The compounds of formula A, as described and claimed, are intended to embrace all such isomeric forms. Accordingly, the examples included herein are to be understood as illustrative of particular mixtures of geometric isomers or single geometric isomers and not as limitations upon the scope of the invention.

The Examples which follow further illustrate the invention. All temperatures are in degrees Centigrade, unless otherwise stated.

EXAMPLE 1

Preparation of
N-methyl-1,5-dimethoxycyclohexa-1,4-diene-3-ethylamine 185.2 g. of N-methyl-(3,5-dimethoxyphenyl)-ethylamine hydrochloride was dissolved in 1600 ml. of water and the solution was made alkaline with 160 ml. of ammonium hydroxide. The mixture was extracted with 3×1000 ml. of dichloromethane and the combined extracts were washed with 1000 ml. of brine and dried over anhydrous sodium sulfate. Evaporation of the solvent on a rotary evaporator at 35°–40° gave 156.0 g. of free base.

In a 12 l. 3-neck flask equipped with a mechanical stirrer and two dry ice condensers, one fitted with a gas inlet and the other with a soda-lime drying tube was condensed 4.0 l. of anhydrous ammonia. To the ammonia was added a solution of 156.0 g. of the free base in 400 ml. of t-butanol and 400 ml. of anhydrous ether over 15 minutes. To the stirred solution was added over 50 min. a total of 33.6 g. of lithium wire cut into 2.5 in. lengths. The addition rate was controlled so that 5 in. of wire was added per minute. After all the lithium had been added, the deep blue mixture was stirred under reflux for 2 hours. Then 2.8 l. of anhydrous ether was added to dilute the mixture, the drying tube was removed to allow the hydrogen to vent, and a total of 280 g. of ammonium chloride powder was added slowly over 30 minutes until the blue color had dissipated. The dry ice condenser was removed and the mixture was stirred and the ammonia allowed to evaporate overnight. To the residue was added 2.8 l. of ice water. The mixture was transferred to a separatory funnel, rinsing with 800 ml. of ether, and the layers were separated. The aqueous layer was extracted with 2×1.5 l. of dichloromethane and the extracts were combined and washed with 1 l. of brine and dried over anhydrous sodium sulfate. Evaporation of the solvents on a rotary evaporator at 40° and finally at 40°/1.0 mm. for 1.5 hours afforded 150.7 g. of crude product as a yellow oil. The crude oil was distilled through a 12-in. Goodloe column (bath 150°) collecting fractions as follows:

| Fraction | bp | wt | gc purity |
| --- | --- | --- | --- |
| 1 | 40–80°/0.45 mm. | 7.9 g. | 4.6% |
| 2 | 80–85°/0.45 to 0.15 mm. | 6.2 g. | 50% |
| 3 | 85–86°/0.15 mm. | 21.2 g. | 92% |
| 4 | 86–87°/0.15 mm. | 99.4 g. | 100% |

Fractions 3 and 4 combined afforded 120.6 g. of N-methyl-1,5-dimethoxycyclohexa-1,4-diene-3-ethylamine as a colorless oil.

Anal. Calcd. for $C_{11}H_{19}NO_2$: C, 66.97; H, 9.71; N, 7.10. Found: C, 66.84; H, 9.62; N, 6.93.

EXAMPLE 2

Preparation of
1,2,3,5,6,7,8,9-octahydro-2-[2-(methylamino)ethyl]-4H-carbazol-4-one A mixture of 15.6 g. of N-methyl-1,5-dimethoxycyclohexa-1,4-diene-3-ethylamine (79 mmol), 16.7 g. of 2-isonitrosocyclohexanone (131 mmol), and 19.5 g. of zinc dust (300 mg-atom) in 300 ml. of 70% aqueous acetic acid heated to reflux for 5 hours, and was cooled and filtered. The filtrate was concentrated in vacuo and excess dioxane was added. The dioxane-acetic acid azeotrope was distilled off and the process was repeated until all the acetic acid was removed. The residue was chromatographed on Alumina III eluting with 10% methanol in dichloromethane to give 10.7 g. of crude 1,2,3,5,6,7,8,9-octahydro-2-[2-(methylamino)ethyl]-4H-carbazol-4-one. The crude product was dissolved in methanol and treated with methanolic HCl and the solvent evaporated to give 12.2 g. of 1,2,3,5,6,7,8,9-octahydro-2-[2-(methylamino)ethyl]-4H-carbazol-4-one hydrochloride.

EXAMPLE 3

Preparation of
2-methyl-2,3,4,4a,5,7,8,9,10,11a-decahydro-4a,11a-trans-1H,6H-cyclohexa[4,5]pyrrolo[2,3-g]isoquinolin-11(11H)-one A mixture of 2.3 g. of 1,2,3,5,6,7,8,9-octahydro-2-[2-(methylamino)ethyl]-4H-carbazol-4-one hydrochloride (8.14 mmol) and 2.3 g. of paraformaldehyde (76 mmol) in 100 ml. of n-butanol was heated in a pressure bottle immersed in a 180° C. oil bath to an internal pressure of 80 psi for 1 hour. The solution was cooled and the solvent was removed at reduced pressure and the residue was dissolved in water and washed with dichloromethane (discarded). The aqueous solution was made alkaline with ammonium hydroxide and extracted with dichloromethane. The extracts were dried over sodium sulfate, filtered, and evaporated to a 10 ml. volume. The mixture was slurried with 10 g. of alumina, filtered, and evaporated to dryness. The residue was chromatographed on 80 g. of Alumina III eluting with 10% methanol in dichloromethane to give crude 2-methyl-2,3,4,4a,5,7,8,9,10,11a-decahydro-4a,11a-trans-1H,6H-cyclohexa[4,5]pyrrolo[2,3-g]isoquinolin-11(11H)-one containing a small amount of the corresponding 4a,11a-cis isomer. Crystallization of the crude product from methanol-dichloromethane-ether gave 2-methyl-2,3,4,4a,5,7,8,9,10,11a-decahydro-4a,11a-trans-1H,6H-cyclohexa[4,5]pyrrolo[2,3-g]isoquinolin-11(11H)-one as an off-white solid. The free base was treated with HCl in methanol and the hydrochloride recrystallized twice from ethanol to give 0.46 g. of pure 2-methyl-2,3,4,4a,5,7,8,9,10,11a-decahydro-4a,11a-trans-1H,6H-cyclohexa[4,5]pyrrolo[2,3-g]isoquinolin-11(11H)-one, hydrochloride, 0.75 molar hydrate as crystals, mp 217°–220° (19% yield).

Anal. Calcd. for $C_{16}H_{22}N_2O \cdot HCl \cdot 0.75H_2O$: C, 62.33; H, 8.01; N, 9.09; Cl, 11.50. Found: C, 62.56; H, 8.11; N, 9.08; Cl, 11.59.

EXAMPLE 4

Preparation of
3,4-dihydro-1H-6,8-dimethoxy-2-methyl-isoquinoline, hydrochloride A solution of N-methyl-(3,5-dimethoxyphenyl)ethylamine hydrochloride (15.0 g, 64.7 mmol) in 30 ml. of water was treated with 35 ml. of 2 N sodium hydroxide and extracted with dichloromethane. The combined extracts were concentrated on a rotary evaporator and mixed with aqueous formaldehyde (65 ml, 37% solution). The mixture was refluxed for 2 hours, made alkaline with 2 N sodium hydroxide (15 ml.) and extracted with dichloromethane. The combined extracts were washed with brine and dried over anhydrous magnesium sulfate and concentrated to give the product as a yellow oil (15.5 g). The oil was dissolved in 100 ml. of ethanol and treated with ethanolic hydrogen chloride. Either (75 ml) was added, and the salt crystallized to give 10.15 g. of 3,4-dihydro-1H-6,8-dimethoxy-2-methylisoquinoline, hydrochloride (64% yield).

EXAMPLE 5

Preparation of
1,2,3,4,4a,7-hexahydro-6,8-dimethoxy-2-methylisoquinoline and
octahydro-2-methylisoquinolin-6,8-dione Ammonia (150 ml) was condensed in a flask containing t-butanol (9.1 g, 123 mmol) and diethyl ether (50 ml). To the solution was added 3,4-dihydro-1H-6,8-dimethoxy-2-methylisoquinoline hydrochloride (1.0 g, 4.1 mmol). After stirring 2-3 minutes, lithium wire (0.57 g, 82 mmol) was added in short pieces over 30 minutes. The blue solution was stirred under reflux for 2.5 hours and solid ammonia chloride (4.5 g) was added until the blue color dissipated. Ether (100 ml) was added and the ammonia was allowed to evaporate overnight. Ice water (100 ml) was added and the organic phase was separated. The aqueous layer was extracted with ethyl acetate and chloroform. The combined extracts were washed with brine and dried over anhydrous magnesium sulfate and concentrated to give 1,2,3,4,4a,7-hexahydro-6,8-dimethoxy-2-methylisoquinoline (0.58 g, crude) as a yellow oil.

The crude product (1.05 g) in 20 ml. of 70% aqueous acetic acid was refluxed for 5 hours and the acetic acid was removed on a rotary evaporator. The residue was dissolved in water and washed with chloroform. The aqueous phase was concentrated to a 10 ml. volume and chromatographed on Dowex AG 50 WX8 eluting with 2 molar aqueous pyridine to afford 0.11 g. of octahydro-2-methylisoquinolin-6,8-dione (11.6% yield) as a light yellow solid. Treatment with hydrochloric acid in methanol afforded the hydrochloride, mp 193°-196°.

EXAMPLE 6

Preparation of
2-methyl-2,3,4,4a,5,7,8,9,10,11a-decahydro-4a,11a-trans-1H,6H-cyclohexa[4,5]pyrrolo[2,3-g]isoquinolin-11(11H)-one via
octahydro-2-methylisoquinolin-6,8-dione A mixture of 72 g. of crude octahydro-2-methylisoquinolin-6,8-dione (about 30% pure, approximately 0.1 mol), 21.1 g. of crude 2-isonitrosocyclohexanone (about 60% pure, approximately 0.1 mol), and 19.5 g. of zinc dust (0.3 g-atom) in 500 ml. of 70% aqueous acetic acid was heated to reflux for 1 hour. A second 10.5 g. portion of 2-isonitrosocyclohexanone and 6.5 g. of zinc dust was added and the mixture refluxed an additional 2 hours. The solution was cooled, filtered and concentrated in vacuo, and the residue was dissolved in water and washed with chloroform (discarded). The aqueous solution was made alkaline with ammonium hydroxide and was extracted with chloroform. The extracts were washed with brine, dried over sodium sulfate, and concentrated. The crude 2-methyl-2,3,4,4a,5,7,8,9,10,11a-decahydro-4a,11a-trans-1H,6H-cyclohexa[4,5]pyrrolo[2,3-g]isoquinolin-11,11H-one was chromatographed on silica gel (dry column) eluting with the organic phase of a mixture prepared by shaking (by volume) 90 parts chloroform, 30 parts methanol, 10 parts water, and 6 parts acetic acid to give 7.8 g. of 2-methyl-2,3,4,4a,5,7,8,9,10,11a-decahydro-4a,11a-trans-1H,6H-cyclohexa[4,5]pyrrolo[2,3-g]isoquinolin-11(11H)-one as a white amorphous solid after slurrying with hot ethanol, mp 273°-275° C. (dec.).

Anal. Calcd. for $C_{16}H_{22}N_2O$: C, 74.38; H, 8.58; N, 10.84. Found: C, 74.21; H, 8.39; N, 10.61.

EXAMPLE 7

Following the procedure of Example 6, starting from 2-isonitrosocyclopentanone and octahydro-2-methylisoquinolin-6,8-dione, there was obtained 2-methyl-1,2,3,4,4a,5,7,8,9,10a-decahydro-4a,10a-trans-6H-cyclopenta[4,5]pyrrolo[2,3-g]isoquinolin-10(10H)-one, mp 296°-297° C. (dec.), crystallized from ethanol-methanol.

Anal. Calcd. for $C_{15}H_{20}N_2O$: C, 73.74; H, 8.25; N, 11.47. Found: C, 73.93; H, 8.41; N, 11.46.

The hydrochloride crystallized from water as a hemihydrate, mp 256°-258° C. (dec.)

Anal. Calcd. for $C_{15}H_{20}N_2O \cdot HCl \cdot 0.5H_2O$: C, 62.17; H, 7.65; N, 9.67; Cl, 12.23. Found: C, 62.16; H, 7.71; N, 9.54; Cl, 12.37.

EXAMPLE 8

Following the procedure of Example 6, starting from 2-isonitrosocycloheptanone and octahydro-2-methylisoquinolin-6,8-dione, there was obtained 2-methyl-1,2,3,4,4a,5,7,8,9,10,11,12a-dodecahydro-4a,12a-trans-6H-cyclohepta[4,5]pyrrolo[2,3-g]iso quinolin-12(12H)-one, mp 293°-296° C., crystallized from ethanol.

Anal. Calcd. for $C_{17}H_{24}N_2O$: C, 74.96; H, 8.88; N, 10.28. Found: C, 74.79; H, 8.74; N, 10.33.

EXAMPLE 9

Following the procedure of Example 6, starting from 2-isonitrosocyclooctanone and octahydro-2-methylisoquinolin-6,8-dione, there was obtained 2-methyl-2,3,4,4a,5,7,8,9,10,11,12,13a-dodecahydro-4a,13a-trans-1H,6H-cycloocta[4,5]pyrrolo[2,3-g]isoquinolin-13(13H)-one, mp 298°-300° C., crystallized from water-dimethylformamide.

Anal. Calcd. for $C_{18}H_{26}N_2O$: C, 75.48; H, 9.15; N, 9.78. Found: C, 75.29; H, 9.04; N, 9.70.

EXAMPLE 10

Preparation of
2,3,4,4a,5,7,8,9,10,11a-decahydro-4a,11a-trans-1H,6H-cyclohexa[4,5]pyrrolo[2,3-g]isoquinolin-11(11H)-one A mixture of 1.9 g. of 2-methyl-2,3,4,4a,5,7,8,9,10,-11a-decahydro-4a,11a-trans-1H,6H-cyclohexa[4,5]pyrrolo[2,3-g]isoquinolin-11(11H)-one, 2.6 g. of ethyl chloroformate, and 3.2 g. of potassium bicarbonate in 100 ml. of dioxane was heated to reflux for 6 hours, cooled, and filtered. The filtrate was concentrated at reduced pressure, dissolved in chloroform, and extracted with 5% aqueous hydrochloric acid, washed with water, brine, and dried over sodium sulfate. Evaporation of the solvent afforded 1.4 g. of the carbamate, 2-ethoxycarbonyl-2,3,4,4a,5,7,8,9,10,11a-decahydro-4a,11a-trans-1H,6H-cyclohexa[4,5]pyrrolo[2,3-g]isoquinolin-11(11H)-one. From the aqueous extracts, 0.45 g. of starting material was recovered by treatment with ammonium hydroxide and chloroform extraction.

The crude carbamate (1.4 g.) was heated to reflux for 24 hours with 15 ml. of 30% aqueous sodium hydroxide in a mixture of 15 ml. of ethanol and 5 ml. of dioxane. The mixture was concentrated in vacuo and the residue was dissolved in 5% aqueous hydrochloric acid and washed with chloroform. The aqueous solution was made alkaline with ammonium hydroxide and extracted with chloroform. The extracts were washed with brine, dried, and concentrated to afford 0.65 g. of 2,3,4,4a,5,7,8,9,10,11a-decahydro-4a,11a-trans-1H,6H-cyclohexa[4,5]pyrrolo[2,3-g]isoquinolin-11(11H)-one.

EXAMPLE 11

Following the procedure of Example 10, starting from 2-methyl-1,2,3,4,4a,5,7,8,9,10a-decahydro-4a,10a-trans-6H-cyclopenta[4,5]pyrrolo[2,3-g]isoquinolin-10(10H)-one, there was obtained via the carbamate, 1,2,3,4,4a,5,7,8,9,10a-decahydro-4a,10a-trans-6H-cyclopenta[4,5]pyrrolo[2,3-g]isoquinolin-10(10H)-one, mp 242°–245° C. (dec.), crystallized from ethanol-ethyl acetate.

Anal. Calcd. for $C_{14}H_{18}N_2O$: C, 73.01; H, 7.88; N, 12.16. Found: C, 72.84; H, 7.78; N, 12.30.

EXAMPLE 12

Following the procedure of Example 10, starting from 2-methyl-2,3,4,4a,5,7,8,9,10,11,12,13a-dodecahydro-4a,13a-trans-1H,6H-cycloocta[4,5]pyrrolo[2,3-g]isoquinolin-13(13H)-one, there was obtained via the carbamate, 1,2,3,4,4a,5,6,7,8,9,10,11,12,13a-tetradecahydro-4a,13a-trans-cycloocta[4,5]pyrrolo[2,3-g]isoquinolin-4-one, mp 283°–5° C., crystallized from ethanol.

Anal. Calcd. for $C_{17}H_{24}N_2O$: C, 74.96; H, 8.88; N, 10.28. Found: C, 74.71; H, 8.65; N, 10.24.

EXAMPLE 13

Preparation of 2-[4-(4-fluorophenyl)-4-oxobutyl]-2,3,4,4a,5,7,8,9,10,11a-decahydro-4a,11a-trans-1H,6H-cyclohexa[4,5]pyrrolo[2,3-g]isoquinolin-11(11H)-one A mixture of 0.68 g. of 2,3,4,4a,5,7,8,9,10,11a-decahydro-4a,11a-trans-1H,6H-cyclohexa[4,5]pyrrolo[2,3-g]isoquinolin-11(11H)-one, 1.68 g. of γ-chloro-p-fluorobutyrophenone, and 1.55 g. of potassium carbonate in 15 ml. of diethylketone was heated to reflux for 24 hours. The mixture was cooled, filtered and concentrated. The residue was chromatographed (dry column) eluting with the organic phase of a mixture prepared by shaking (by volume) 90 parts chloroform, 30 parts methanol, 10 parts water, and 6 parts acetic acid to afford 0.85 g. of a crude amine, which was recrystallized from ethanol to afford 0.42 g. of pure 2-[4-(4-fluorophenyl)-4-oxobutyl]-2,3,4,4a,5,7,8,9,10,11a-decahydro-4a,11a-trans-1H,6H-cyclohexa[4,5]pyrrolo[2,3-g]isoquinolin-11(11H)-one as a crystalline solid, mp 220°–222°.

Anal. Calcd. for $C_{25}H_{29}N_2O_2F$: C, 73.50; H, 7.16; N, 6.86; F, 4.65. Found: C, 73.46; H, 7.08; N, 7.16; F, 4.61.

EXAMPLE 14

Following the procedure of Example 13, alkylation of 2,3,4,4a,5,7,8,9,10,11a-decahydro-4a,11a-trans-1H,6H-cyclohexa[4,5]pyrrolo[2,3-g]isoquinolin-11(11H)-one with (2-bromoethyl)benzene afforded 2-(2-phenylethyl)-2,3,4,4a,5,7,8,9,10,11a-decahydro-4a,11a-trans-1H,6H-cyclohexa[4,5]pyrrolo[2,3-g]isoquinolin-11(11H)-one, mp 250°–256° C. (dec.), as a crystalline solid after recrystallization from ethanol.

Anal. Calcd. for $C_{23}H_{28}N_2O$: C, 79.27; H, 8.10; N, 8.04. Found: C, 79,29; H, 8.40; N, 7.97.

EXAMPLE 15

Following the procedure of Example 13, alkylation of 2,3,4,4a,5,7,8,9,10,11a-decahydro-4a,11a-trans-1H,6H-cyclohexa[4,5]pyrrolo[2,3-g]isoquinolin-11(11H)-one with benzyl chloride afforded 2-benzyl-2,3,4,4a,5,7,8,9,10,11a-decahydro-4a,11a-trans-1H,6H-cyclohexa[4,5]pyrrolo[2,3-g]isoquinolin-11(11H)-one, mp 266°–268° C., as a crystalline solid after recrystallization from ethanol.

Anal. Calcd. for $C_{22}H_{26}N_2O$: C, 79.00; H, 7.84; N, 8.38. Found: C, 79.27; H, 8.03; N, 8.60.

EXAMPLE 16

Following the procedure of Example 13, alkylation of 1,2,3,4,4a,5,7,8,9,10a-decahydro-4a,10a-trans-6H-cyclopenta[4,5]pyrrolo[2,3-g]isoquinolin-10(10H)-one with benzyl chloride afforded 2-benzyl-1,2,3,4,4a,5,7,8,9,10a-decahydro-4a,10a-trans-6H-cyclopenta[4,5]pyrrolo[2,3-g]isoquinolin-10(10H)-one, mp 258°–260° C. (dec.), as a crystalline solid after recrystallization from ethanol.

Anal. Calcd. for $C_{21}H_{24}N_2O$: C, 78.71; H, 7.55; N, 8.74. Found: C, 78.97; H, 7.54; N, 8.63.

EXAMPLE 17

Following the procedure of Example 13, alkylation of 1,2,3,4,4a,5,7,8,9,10a-decahydro-4a,10a-trans-6H-cyclopenta[4,5]pyrrolo[2,3-g]isoquinolin-10(10H)-one with γ-chloro-p-fluorobutyrophenone afforded 2-[4-(4-fluorophenyl)-4-oxobutyl]-1,2,3,4,4a,5,7,8,9,10a-decahydro-4a,10a-trans-6H-cyclopenta[4,5]pyrrolo[2,3-g]isoquinolin-10(10H)-one, mp 225°–227° C., as a crystalline solid after recrystallization from ethanol.

Anal. Calcd. for $C_{24}H_{27}FN_2O_2$: C, 73.07; H, 6.90; N, 7.10; F, 4.82. Found: C, 72.76; H, 6.86; N, 7.24; F, 4.71.

EXAMPLE 18

Following the procedure of Example 13, alkylation of 1,2,3,4,4a,5,7,8,9,10a-decahydro-4a,10a-trans-6H-cyclopenta[4,5]pyrrolo[2,3-g]isoquinolin-10(10H)-one with (2-bromoethyl)benzene afforded 2-(2-phenylethyl)-1,2,3,4,4a,5,7,8,9,10a-decahydro-4a,10a-trans-6H-cyclopenta[4,5]pyrrolo[2,3-g]isoquinolin-10(10H)-one, mp 251°–254° C. (dec.), as a crystalline solid after recrystallization from ethanol.

Anal. Calcd. for $C_{22}H_{26}N_2O$: C, 79.00; H, 7.84; N, 8.38. Found: C, 78.68; H, 7.72; N, 8.28.

EXAMPLE 19

Following the procedure of Example 13, alkylation of 1,2,3,4,4a,5,7,8,9,10a-decahydro-4a,10a-trans-6H-cyclopenta[4,5]pyrrolo[2,3-g]isoquinolin-10(10H)-one with 4-methoxybenzyl chloride afforded 2-(4-methoxybenzyl)-1,2,3,4,4a,5,7,8,9,10a-decahydro-4a,10a-trans-6H-cyclopenta[4,5]pyrrolo[2,3-g]isoquinolin-4-one, mp 236°–8° (dec.), as a crystalline solid after recrystallization from ethanol.

Anal. Calcd. for $C_{22}H_{26}N_2O_2$: C, 75.40; H, 7.48; N, 7.99. Found: C, 75.39; H, 7.41; N, 8.03.

EXAMPLE 20

Following the procedure of Example 13, alkylation of 1,2,3,4,4a,5,7,8,9,10a-decahydro-4a,10a-trans-6H-cyclopenta[4,5]pyrrolo[2,3-g]isoquinolin-10(10H)-one with 4-chlorobenzyl chloride afforded 2-(4-chlorobenzyl)-1,2,3,4,4a,5,7,8,9,10a-decahydro-4a,10a-trans-6H-cyclopenta[4,5]pyrrolo[2,3-g]isoquinolin-10(10H)-one as a crystalline monohydrate, mp 254°-6° after recrystallization from ethanol.

Anal. Calcd. for $C_{21}H_{23}N_2O$ Cl $H_2O$: C, 67.63; H, 6.22; N, 7.51; Cl, 9.51. Found: C, 67.86; H, 6.38; N, 7.50; Cl, 9.92.

EXAMPLE 21

Following the procedure of Example 13, alkylation of 1,2,3,4,4a,5,7,8,9,10a-decahydro-4a,10a-trans-6H-cyclopenta[4,5]pyrrolo[2,3-g]isoquinolin-10(10H)-one with allyl bromide afforded 2-(2-propenyl)-1,2,3,4,4a,5,7,8,9,10a-decahydro-4a,10a-trans-6H-cyclopenta[4,5]pyrrolo[2,3-g]isoquinolin-10(10H)-one, mp 257°-9° (dec.), after recrystallization from ethyl acetate-ethanol.

Anal. Calcd. for $C_{17}H_{22}N_2O$: C, 75.52; H, 8.20; N, 10.36. Found: C, 75.25; H, 8.17; N, 10.36.

EXAMPLE 22

Following the procedure of Example 12, alkylation of 1,2,3,4,4a,5,7,8,9,10a-decahydro-4a,10a-trans-6H-cyclopenta[4,5]pyrrolo[2,3-g]isoquinolin-10(10H)-one with 2-bromoethyl ether afforded 2-(2-ethoxyethyl)-1,2,3,4,4a,5,7,8,9,10a-decahydro-4a,10a-trans-6H-cyclopenta[4,5]pyrrolo[2,3-g]isoquinolin-10(10H)-one, mp 236°-8° (dec.) as a crystalline solid after recrystallization from ethanol.

Anal. Calcd. for $C_{18}H_{26}N_2O_2$: C, 71.49; H, 8.67; N, 9.26. Found: C, 71.35; H, 8.47; N, 9.23.

EXAMPLE 23

Following the procedure of Example 13, alkylation of 2,3,4,4a,5,7,8,9,10,11,12,13a-dodecahydro-4a,13a-trans-1H,6H-cycloocta[4,5]pyrrolo[2,3-g]isoquinolin-13(13H)-one with the ethylene ketal of gamma-chloro-p-fluorobutyrophenone followed by acid hydrolysis afforded 2-[4-(4-fluorophenyl)-4-oxobutyl]-1,2,3,4,4a,5,6,7,8,9,10,11,12,13a-tetradecahydro-4a,13a-trans-cycloocta[4,5]pyrrolo[2,3-g]isoquinolin-13(13H)-one.

EXAMPLE 24

Following the procedure of Example 13, the compounds listed in Table I may be prepared from the indicated cycloalka[4,5]pyrrolo[2,3-g]isoquinoline and the indicated halide.

TABLE I

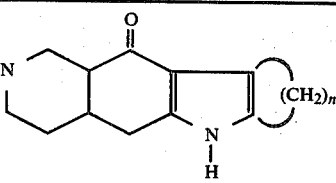

| Example | Name | n | $R_2$ | X |
|---|---|---|---|---|
| 24 | 2-ethyl-1,2,3,4,4a,5,7,8,9,10a-decahydro-4a,10a-trans-6H—cyclopenta[4,5]pyrrolo[2,3-g]isoquinolin-10(10H)—one | 3 | $CH_3CH_2-$ | Br |
| 25 | 2-(2-acetoxyethyl)-1,2,3,4,4a,5,7,8,9,10a-decahydro-4a,10a-trans-6H—cyclopenta[4,5]pyrrolo[2,3-g]isoquinolin-10(10H)—one | 3 | $CH_3COCH_2CH_2-$ (with C=O) | Br |
| 26 | 2-[3-(4-fluorophenyl)-3-oxopropyl]-1,2,3,4,4a,5,7,8,9,10a-decahydro-4a,10a-trans-6H—cyclopenta[4,5]pyrrolo-[2,3-g]isoquinolin-10(10H)—one | 3 | 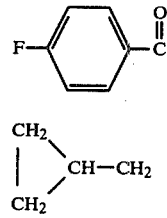 | Cl |
| 27 | 2-cyclopropylmethyl-1,2,3,4,4a,5,7,8,9,10a-decahydro-4a,10a-trans-6H—cyclopenta[4,5]pyrrolo[2,3-g]isoquinolin-10(10H)—one | 3 | cyclopropyl-$CH_2-$ | Cl |
| 28 | 2-propargyl-1,2,3,4,4a,5,7,8,9,10a-decahydro-4a,10a-trans-6H—cyclopenta[4,5]pyrrolo[2,3-g]isoquinolin-10(10H)—one | 3 | $HC{\equiv}C-CH_2-$ | Br |
| 29 | 2-[2-(2-thienyl)ethyl]-1,2,3,4,4a,5,7,8,9,10a-decahydro-4a,10a-trans-6H—cyclopenta[4,5]pyrrolo[2,3-g]isoquinolin-10(10H)—one | 3 | 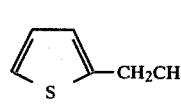 | Br |
| 30 | 2-[2-(2-furyl)ethyl]-1,2,3,4,4a,5,7,8,9,10a-decahydro-4a,10a-trans-6H—cyclopenta[4,5]pyrrolo[2,3-g]isoquinolin-10(10H)—one | 3 | 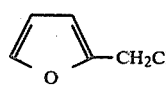 | Br |
| 31 | 2-[2-(2,3-dihyro-2-oxo-1H—benzimidazol-l-yl)ethyl]-1,2,3,4,4a,5,7,8,9,10a-decahydro-4a,10a-trans-6H—cyclopenta[4,5]pyrrolo[2,3-g]isoquinolin-10(10H)—one | 3 | 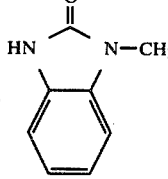 | Br |

TABLE I-continued

[Reaction scheme: starting tricyclic ketone with H—N and pyrrole NH + (CH$_2$)$_n$ + R$_2$—X →(K$_2$CO$_3$)→ N-substituted product with R$_2$—N]

| Example | Name | n | R$_2$ | X |
|---|---|---|---|---|
| 32 | 2-[2-(benzyloxy)ethyl]-1,2,3,4,4a,5,7,8,9,10a-decahydro-4a,10a-trans-6H—cyclopenta[4,5]pyrrolo[2,3-g]isoquinolin-10(10H)—one | 3 | C$_6$H$_5$—CH$_2$OCH$_2$CH$_2$— | Br |
| 33 | 2-(3-phenyl-2-propenyl)-1,2,3,4,4a,5,7,8,9,10a-decahydro-4a,10a-trans-6H—cyclopenta[4,5]pyrrolo[2,3-g]isoquinolin-10(10H)—one | 3 | C$_6$H$_5$—CH=CH—CH$_2$— | Br |
| 34 | 2-[2-(ethenyloxy)ethyl]-1,2,3,4,4a,5,7,8,9,10a-decahydro-4a,10a-trans-6H—cyclopenta[4,5]pyrrolo[2,3-g]isoquinolin-10(10H)—one | 3 | CH$_2$=CH—O—CH$_2$CH$_2$— | Br |
| 35 | 2-(2-ethoxyethyl)-2,3,4,4a,5,7,8,9,10,11a-decahydro-4a,11a-trans-1H,6H—cyclohexa[4,5]pyrrolo[2,3-g]isoquinolin-11(11H)—one | 4 | CH$_3$CH$_2$OCH$_2$CH$_2$— | Br |
| 36 | 2-cyclobutylmethyl-2,3,4,4a,5,7,8,9,10,11a-decahydro-4a,11a-trans-1H,6H—cyclohexa[4,5]pyrrolo[2,3-g]isoquinolin-11(11H)—one | 4 | cyclobutyl-CH$_2$— | Br |
| 37 | 2-[2-(2-thienyl)ethyl]-2,3,4,4a,5,7,8,9,10,11a-decahydro-4a,11a-trans-1H,6H—cyclohexa[4,5]pyrrolo[2,3-g]isoquinolin-11(11H)—one | 4 | 2-thienyl-CH$_2$CH$_2$— | Br |
| 38 | 2-[2-(2-furyl)ethyl]-2,3,4,4a,5,7,8,9,10,11a-decahydro-4a,11a-trans-1H,6H—cyclohexa[4,5]pyrrolo[2,3-g]isoquinolin-11(11H)—one | 4 | 2-furyl-CH$_2$CH$_2$— | Br |
| 39 | 2-[3-(4-fluorophenyl)-3-oxopropyl]-2,3,4,4a,5,7,8,9,10,11a-decahydro-4a,11a-trans-1H,6H—cyclohexa[2,3-g]pyrrolo[2,3-g]isoquinolin-11(11H)—one | 4 | 4-F-C$_6$H$_4$—C(O)CH$_2$CH$_2$— | Cl |
| 40 | 2-(2-propenyl)-2,3,4,4a,5,7,8,9,10,11a-decahydro-4a,11a-trans-1H,6H—cyclohexa[4,5]pyrrolo[2,3-g]isoquinolin-11(11H)—one | 4 | CH$_2$=CH—CH$_2$— | Br |
| 41 | 2-(3-phenoxypropyl)-2,3,4,4a,5,7,8,9,10,11a-decahydro-4a,11a-trans-1H,6H—cyclohexa[4,5]pyrrolo[2,3-g]isoquinolin-11(11H)—one | 4 | C$_6$H$_5$—OCH$_2$CH$_2$CH$_2$ | Br |
| 42 | 2-[3-(2,3-dihydro-2-oxo-1H—benzimidazol-1-yl)propyl]-2,3,4,4a,5,7,8,9,10,11a-decahydro-4a,11a-trans-1H,6H—cyclohexa[4,5]pyrrolo[2,3-g]isoquinolin-11(11H)—one | 4 | (2-oxo-benzimidazol-1-yl)—CH$_2$CH$_2$CH$_2$— | Br |
| 43 | 2-[4-(4-fluorophenyl)-4-oxobutyl]-1,2,3,4,4a,5,7,8,9,10,11,12a-dodecahydro-4a,12a-trans-6H—cyclohepta[4,5]pyrrolo[2,3-g]isoquinolin-12(12H)—one | 5 | 4-F-C$_6$H$_4$—C(O)CH$_2$CH$_2$CH$_2$— | Cl |
| 44 | 2-(3-phenoxypropyl)-1,2,3,4,4a,5,7,8,9,10,11,12a-dodecahydro-4a,12a-trans-6H—cyclohepta[4,5]pyrrolo[2,3-g]-isoquinolin-12(12H)—one | 5 | C$_6$H$_5$—OCH$_2$CH$_2$CH$_2$— | Br |

TABLE I-continued

[Structure: Reaction scheme showing starting material (with H-N on left ring) + (CH₂)ₙ + R₂—X with K₂CO₃ giving product (with R₂-N on left ring) + (CH₂)ₙ]

| Example | Name | n | R₂ | X |
|---|---|---|---|---|
| 45 | 2-(2-phenylethyl)-1,2,3,4,4a,5,7,8,9,10,11,12a-dodecahydro-4a,12a-trans-6H—cyclohepta[4,5]pyrrolo[2,3-g]isoquinolin-12(12H)—one | 5 | C₆H₅—CH₂CH₂— | Br |
| 46 | 2-(2-phenylethyl)-2,3,4,4a,5,7,8,9,10,11,12,13a-dodecahydro-4a,13a-trans-1H,6H—cycloocta[4,5]pyrrolo[2,3-g]isoquinolin-13(13H)—one | 6 | C₆H₅—CH₂CH₂— | Br |
| 47 | 2-(2-ethoxyethyl)-2,3,4,4a,5,7,8,9,10,11,12,13a-dodecahydro-4a,13a-trans-1H,6H—cycloocta[4,5]pyrrolo[2,3-g]isoquinolin-13(13H)—one | 6 | CH₃CH₂OCH₂CH₂— | Br |
| 48 | 2-(3-phenoxypropyl)-2,3,4,4a,5,7,8,9,10,11,12,13a-dodecahydro-4a,13a-trans-1H,6H—cycloocta[4,5]pyrrolo[2,3-g]isoquinolin-13(13H)—one | 6 | C₆H₅—OCH₂CH₂CH₂— | Br |

EXAMPLE 49

Preparation of 2-methyl-1,2,3,4,4a,5,7,8,9,10a-decahydro-4a,10a-trans-6H-cyclopenta[4,5]pyrrolo[2,3-g]isoquinolin-10(10H)-thione A mixture of 244 mg. (1.0 mmol) of 2-methyl-1,2,3,4,4a,5,7,8,9,10a-decahydro-4a,10a-trans-6H-cyclopenta[4,5]pyrrolo[2,3-g]isoquinolin-10(10H)-one and 222 mg. (1.0 mmol) of phosphorus pentasulfide in 15 ml. of dioxane was stirred and refluxed for 17 hours. The dioxane solution was decanted off and water (20 ml.) and enough ammonium hydroxide to bring the pH to 8-9 was added to the residue. The mixture was extracted with chloroform, and the extracts were washed with brine, dried and evaporated. The crude thione was chromatographed as described in Example 13 to afford 65 mg. of pure solid thione which was recrystallized from acetonitrile to give 2-methyl-1,2,3,4,4a,5,7,8,9,10a-decahydro-4a,10a-trans-6H-cyclopenta[4,5]pyrrolo[2,3-g]isoquinolin-10(10H)-thione, mp 224°-227° C. (dec.).

Anal. Calcd. for $C_{15}H_{20}N_2S$: C, 69.19; H, 7.74; N, 10.76. Found: C, 68.97; H, 7.59; N, 10.97.

EXAMPLE 50

The procedure of Example 50 is used to prepare 2-methyl-2,3,4,4a,5,7,8,9,10,11a-decahydro-4a,11a-trans-1H,6H-cyclohexa[4,5]pyrrolo[2,3-g]isoquinolin-11(11H)-thione starting from 2-methyl-2,3,4,4a,5,7,8,9,10,11a-decahydro-4a,11a-trans-1H,6H-cyclohexa[4,5]pyrrolo[2,3-g]isoquinolin-11(11H)-one.

EXAMPLE 51

The procedure of Example 50 is used to prepare 1,2,3,4,4a,5,7,8,9,10a-decahydro-4a,10a-trans-6H-cyclopenta[4,5]pyrrolo[2,3-g]isoquinolin-10(10H)-thione starting from 1,2,3,4,4a,5,7,8,9,10a-decahydro-4a,10a-trans-6H-cyclopenta[4,5]pyrrolo[2,3-g]isoquinolin-10(10H)-one.

EXAMPLE 52

The procedure of Example 13 is used to prepare 2-[4-(4-fluorophenyl-4-oxobutyl]1,2,3,4,4a,5,7,8,9,10a-decahydro-4a,10a-trans-6H-cyclopenta[4,5]pyrrolo[2,3-g]isoquinolin-10(10H)-thione starting from 1,2,3,4,4a,5,7,8,9,10a-decahydro-4a,10a-trans-6H-cyclopenta[4,5]pyrrolo[2,3-g]isoquinolin-10(10H)-thione and γ-chloro-p-fluorobutyrophenone.

EXAMPLE 53

The procedure of Example 13 is used to prepare 2-(2-phenylethyl)-1,2,3,4,4a,5,7,8,9,10a-decahydro-4a,10a-trans-6H-cyclopenta[4,5]pyrrolo[2,3-g]isoquinolin-10(10H)-thione starting from 1,2,3,4,4a,5,7,8,9,10a-decahydro-4a,10a-trans-6H-cyclopenta[4,5]pyrrolo[2,3-g]isoquinolin-10(10H)-thione and (2-bromoethyl)benzene.

EXAMPLE 54

Preparation of 6-benzoyl-2-methyl-1,2,3,4,4a,5,7,8,9,10a-decahydro-4a,10a-trans-6H-cyclopenta[4,5]pyrrolo[2,3-g]isoquinoline-10(10H)-one To a mixture of 244 mg. (1.0 mmol) of 2-methyl-1,2,3,4,4a,5,7,8,9,10a-decahydro-4a,10a-trans-6H-cyclopenta[4,5]pyrrolo[2,3-g]isoquinolin-10(10H)-one in 10 ml. of dry tetrahydrofuran at −30° is added 0.5 ml. of n-butyllithium (1.1 mmol of 2.2 M solution in hexane) over 2–3 minutes via syringe. The solution is stirred for 30 minutes at −30° and 168 mg. of benzoyl chloride (1.2 mmol) is added over 2–3 minutes. The solution is stirred 1 hour at −30° and 30 minutes at room temperature. The mixture is poured onto ice and extracted with chloroform. The extracts are washed with brine, dried (sodium sulfate), concentrated and chromatographed to afford the 6-benzoyl-2-methyl-1,2,3,4,4a,5,7,8,9,10a-decahydro-4a,10a-trans-6H-cyclopenta[4,5]pyrrolo[2,3-g]isoquinolin-10(10H)-one.

EXAMPLE 55

Following the procedure of Example 54, 2,6-dimethyl-1,2,3,4,4a,5,7,8,9,10a-decahydro-4a,10a-trans-6H-cyclopenta[4,5]pyrrolo[2,3-g]isoquinolin-10(10H)-one is prepared using methyl iodide instead of benzoyl chloride.

EXAMPLE 56

Preparation of 2-(2-hydroxy-3,3-dimethylbutyl)-2,3,4,4a,5,7,8,9,10,11a-decahydro-4a,11a-trans-1H,6H-cyclohexa[4,5]pyrrolo[2,3-g]isoquinolin-11(11H)-one A solution of 488 mg. (2.0 mmol) of 2,3,4,4a,5,7,8,9,10,11a-decahydro-4a,11a-trans-1H,6H-cyclohexa[4,5]pyrrolo[2,3-g]isoquinolin-11(11H)-one and 300 mg. (3.0 mmol) of 3,3-dimethyl-1,2-epoxybutane in 15 ml. of methanol was refluxed for 24 hours and concentrated. The residue was chromatographed, and the crude product (350 mg.) crystallized from ethanol to give 200 mg. of 2-(2-hydroxy-3,3-dimethylbutyl)-2,3,4,4a,5,7,8,9,10,11a-decahydro-4a,11a-trans-1H,6H-cyclohexa[4,5]pyrrolo[2,3-g]isoquinolin-11(11H)-one, mp 276°–278° C. (dec.).

Anal. Calcd. for $C_{21}H_{32}N_2O_2$: C, 73.22; H, 9.36; N, 8.13. Found: C, 73.39; H, 9.31; N, 8.15.

EXAMPLE 57

The procedure of Example 56 is used to prepare 2-(2-hydroxy-2-phenylethyl)-1,2,3,4,4a,5,7,8,9,10a-decahydro-4a,10a-trans-6H-cyclopenta[4,5]pyrrolo[2,3-g]isoquinolin-10(10H)-one starting from 1,2,3,4,4a,5,7,8,9,10a-decahydro-4a,10a-trans-6H-cyclopenta[4,5]pyrrolo[2,3-g]isoquinolin-10(10H)-one and styrene oxide.

EXAMPLE 58

Following the procedure of Example 56, alkylation of 1,2,3,4,4a,5,7,8,9,10a-decahydro-4a,10a-trans-6H-cyclopenta[4,5]pyrrolo[2,3-g]isoquinolin-10(10H)-one with ethylene oxide at room temperature afforded 2-(2-hydroxyethyl)-1,2,3,4,4a,5,7,8,9,10a-decahydro-4a,10a-trans-6H-cyclopenta[4,5]pyrrolo[2,3-g]isoquinolin-10(10H)-one, mp 237°–9° (dec.) as a crystalline solid after recrystallization from ethanol.

Anal. Calcd. for $C_{16}H_{22}N_2O_2$: C, 70.04; H, 8.08; N, 10.21. Found: C, 69.66; H, 8.17; N, 10.19.

EXAMPLE 59

Following the procedure of Example 56, alkylation of 1,2,3,4,4a,5,7,8,9,10a-decahydro-4a,10a-trans-6H-cyclopenta[4,5]pyrrolo[2,3-g]isoquinolin-10(10H)-one with 3,3-dimethyl-1,2-epoxybutane afforded 2-(2-hydroxy-3,3-dimethylbutyl)-1,2,3,4,4a,5,7,8,9,10a-decahydro-4a,10a-trans-6H-cyclopenta[4,5]pyrrolo[2,3-g]isoquinolin-10(10H)-one, mp 284°–6° (dec.), as a crystalline solid after recrystallization from ethanol.

Anal. Calcd. for $C_{20}H_{30}N_2O_2$: C, 72.69; H, 9.15; N, 8.48. Found: C, 72.80; H, 9.02; N, 8.55.

EXAMPLE 60

A mixture of 30 mg of sodium hydride dispersion (57%, washed free of oil) and 2 ml of dry dimethyl sulfoxide (DMSO) was heated to 65°–70° for 1.5 hrs. The solution was cooled and a solution of 244 mg of 2-methyl-1,2,3,4,4a,5,7,8,9,10a-decahydro-4a,10a-trans-6H-cyclopenta[4,5]pyrrolo[2,3-g]isoquinolin-10(10H)-one in 1 ml of dry DMSO was added in portions. The mixture was stirred for 2 hrs. at room temperature. A solution of 160 mg of benzyl chloride in 1 ml of dry DMSO was added, and the mixture was stirred for 2.5 hrs. at room temperature and then poured into ice water. The mixture was extracted with chloroform, the extracts washed with brine, dried and concentrated to give 560 mg crude solid. Chromatography on silica gel using the system given in Example 62 gave 60 mg of 6-benzyl-2-methyl-1,2,3,4,4a,5,7,8,9,10a-decahydro-4a,10a-trans-6H-cyclopenta[4,5]pyrrolo[2,3-g]isoquinolin-10(10H)-one as a crystalline solid, mp 169°–171° after recrystallization from ethyl acetate-ethanol.

Anal. Calcd. for $C_{22}H_{26}N_2O$: C, 79.00; H, 7.84; N, 8.35. Found: C, 78.92; H, 7.84; N, 8.55.

EXAMPLE 61

To a solution of 2.35 g of rac.-2-methyl-1,2,3,4,4a,5,7,8,9,10a-decahydro-4a,10a-trans-6H-cyclopenta[4,5]pyrrolo[2,3-g]isoquinolin-10(10H)-one in 20 ml of methanol was added a solution of 3.62 g of (+)-dibenzoyl-(D)-tartaric acid monohydrate in 20 ml of methanol. The mixture was concentrated and crystallized from methanol three times and converted to the free base with ammonium hydroxide. Recrystallization of the base from ethanol afforded 0.18 g of (−)-2-methyl-1,2,3,4,4a,5,7,8,9,10a-decahydro-4a,10a-trans-6H-cyclopenta[4,5]pyrrolo[2,3-g]isoquinolin-10(10H-one, mp 270°–2° (dec.). The hydrochloride salt gave $[\alpha]_D^{25} -101.17°$ in methanol (1%).

EXAMPLE 62

Preparation of 2-[4-(4-fluorophenyl)-4-hydroxybutyl]-1,2,3,4,4a,5,7,8,9,10a-decahydro-6H-4a,10a-trans-cyclopenta[4,5]pyrrolo[2,3-g]isoquinolin-10(10H)-one A mixture of 394 mg (1.0 mmol) of 2-[4-(4-fluorophenyl)-4-oxobutyl]-1,2,3,4,4a,5,7,8,9,10a-decahydro-6H-4a,10a-trans-cyclopenta[4,5]pyrrolo[2,3-g]isoquinolin-10(10H)-one and 151 mg of sodium borohydride (4.0 mmol) in 15 ml of ethanol was stirred at room temperature for 24 hours. A second portion of sodium borohydride (150 mg, 4.0 mmol) was added, and the mixture was stirred further at room temperature for 24 hrs. The mixture was poured into 50 ml of water and filtered to remove the white solid product containing some starting material. Dry column chromatography on silica gel eluting with the lower phase of a mixture of 90 ml chloroform, 30 ml methanol, 10 ml water and 6 ml acetic acid afforded 220 mg of solid which was recrystallized from aqueous dimethylformamide to give 2-[4-(4-fluorophenyl)-4-hydroxybutyl]-1,2,3,4,4a,5,7,8,9,10a-decahydro-6H-4a,10a-trans-cyclopenta[4,5]pyrrolo[2,3-g]isoquinolin-10(10H)-one, mp 243°–5°, as a mixture of diastereomers.

Anal. Calcd. for $C_{24}H_{29}N_2O_2F$: C, 72.70; H, 7.37; N, 7.07. Found: C, 72.68; H, 7.56; N, 7.33.

EXAMPLE 63

Following the procedure of Example 62, sodium borohydride reduction of 2-[4-(4-fluorophenyl)-4-oxobutyl]-2,3,4,4a,5,7,8,9,10,11a-decahydro-4a,11a-trans-1H,6H-cyclohexa[4,5]pyrrolo[2,3-g]isoquinolin-11(11H)-one afforded 2-[4-(4-fluorophenyl)-4-hydroxybutyl]-2,3,4,4a,5,7,8,9,10,11a-decahydro-4a,11a-trans-1H,6H-cyclohexa[4,5]pyrrolo[2,3-g]isoquinolin-11(11H)-one, as a mixture of diastereomers, mp 239°–41°, crystallized from 1,4-dioxane.

Anal. Calcd. for C₂₅H₃₁N₂O₂F: C, 73.14; H, 7.61; N, 6.82. Found: C, 73.18; H, 7.72; N, 6.82.

EXAMPLE 64

Following the procedure of Example 62, sodium borohydride reduction of 2-[4-(4-fluorophenyl)-4-oxobutyl]-2,3,4,4a,5,7,8,9,10,11,12,13a-dodecahydro-4a,13a-trans-1H,6H-cycloocta[4,5]pyrrolo[2,3-g]isoquinolin-13(13H)-one afforded 2-[4-(4-fluorophenyl)-4-hydroxybutyl]-2,3,4,4a,5,7,8,9,10,11,12,13a-dodecahydro-4a,13a-trans-1H,6H-cycloocta[4,5]pyrrolo[2,3-g]isoquinolin-13(13H)-one, as a mixture of diastereomers, mp 249°–51°, crystallized from 1,4-dioxane.

Anal. Calcd. for C₂₇H₃₅N₂O₂F: C, 73.94; H, 8.04; L N, 6.39. Found: C, 73.71; H, 8.05; N, 6.37.

EXAMPLE 65

Preparation of
5-[(2-methylamino)ethyl]-cyclohexane-1,3-dione

To a stirred solution of N-methyl-1,5-dimethoxycyclohexa-1,4-diene-3-ethylamine (5.5 g, 27.9 mmol) in 20 ml of tetrahydrofuran was added 10 ml of 6 N hydrochloric acid in one portion. The warm solution was heated for 15 min. at 50° C. and concentrated to give a light yellow oil. The crude oil was dissolved in 25 ml of water, and the solution was mixed with 50 g of Dowex 50×8 resin (previously washed with 2 N HCl and deionized water) in a sintered glass funnel. After a few minutes, the aqueous solution was drawn out by suction, and the resin rinsed with four 50 ml-portions of water, and then with eight 35 ml-portions of 2 M aqueous pyridine. Pyridine fractions 3–8 were pooled and concentrated to give 3.9 g of 5-[(2-methylamino)ethyl]-cyclohexane-1,3-dione. An analytical sample crystallized from water and had mp 171°–4° C.

Anal. Calcd. for C₉H₁₅NO₂: C, 63.88; H, 8.93; N, 8.28. Found: C, 63.50; H, 8.87; N, 8.15.

EXAMPLE 66

Preparation of
6-benzyl-2,3,4,4a,5,7,8,9,10,11a-decahydro-4a,11a-trans-1H,6H-cyclohexa[4,5]pyrrolo[2,3-g]isoquinolin-11(11H)-one Following the procedure of example 60, 316 mg of 2-ethoxycarbonyl-2,3,4,4a,5,7,8,9,10,11a-decahydro-4a,11a-trans-1H,6H-cyclohexa[4,5]pyrrolo[2,3-g]isoquinolin-11(11H)-one was alkylated with 190 mg of benzyl chloride to afford 6-benzyl-2-ethoxycarbonyl-2,3,4,4a,5,7,8,9,10,11a-decahydro-4a,11a-trans-1H,6H-cyclohexa[4,5]pyrrolo[2,3-g]isoquinolin-11(11H)-one (220 mg), mp 54°–60° C., which was hydrolyzed following the procedure of example 10 with sodium hydroxide to afford 80 mg of 6-benzyl-2,3,4,4a,5,7,8,9,10,11a-decahydro-4a,11a-trans-1H,6H-cyclohexa[4,5]pyrrolo[2,3-g]isoquinolin-11(11H)-one. cl EXAMPLE 67

Capsule Formulation

| Ingredients | mg/capsule | | | | |
|---|---|---|---|---|---|
| | 0.1 | 0.5 | 5.0 | 10.0 | 25.0 |
| 2-[4-(4-fluorophenyl)-4-oxobutyl]-1,2,3,4,4a,5,7,8,9,10a-decahydro-4a,10a-trans-6H—cyclopenta[4,5]pyrrolo[2,3-g]isoquinolin-10(10H)—one | 0.1 | 0.5 | 5.0 | 10.0 | 25.0 |
| Lactose | 183.9 | 183.5 | 179.0 | 218.0 | 257.0 |
| Starch | 30.0 | 30.0 | 30.0 | 50.0 | 70.0 |
| Talc | 5.0 | 5.0 | 5.0 | 10.0 | 15.0 |
| Magnesium Stearate | 1.0 | 1.0 | 1.0 | 2.0 | 3.0 |
| Total | 220 mg. | 220 mg. | 220 mg. | 290 mg. | 370 mg. |

Procedure:
Mix 2-[4-(4-fluorophenyl)-4-oxobutyl]-1,2,3,4,4a,5,7,8,9,10a-decahydro-4a,10a-trans-6H—cyclopenta[4,5]pyrrolo[2,3-g]isoquinolin-10(10H)—one, lactose and starch in a suitable mixer. Mill through a suitable mill. Mix with talc and magnesium stearate and fill on capsule machine.

EXAMPLE 68

Tablet Formulation (Direct Compression)

| Ingredients | mg/capsule | | | | |
|---|---|---|---|---|---|
| | 0.1 | 0.5 | 5.0 | 10.0 | 25.0 |
| 2-[4-(4-fluorophenyl)-4-oxobutyl]-1,2,3,4,4a,5,7,8,9,10a-decahydro-4a,10a-trans-6H—cyclopenta[4,5]pyrrolo[2,3-g]isoquinolin-10(10H)—one | 0.1 | 0.5 | 5.0 | 10.0 | 25.0 |
| Lactose | 85.4 | 85.5 | 81.0 | 103.0 | 112.5 |
| Avicel | 30.0 | 30.0 | 30.0 | 45.0 | 60.0 |
| Modified Starch | 8 | 7.5 | 7.5 | 10.0 | 15.0 |
| Magnesium Stearate | 1.5 | 1.5 | 1.5 | 2.0 | 2.5 |
| Total | 125 mg. | 125 mg. | 125 mg. | 170 mg. | 215 mg. |

Procedure:
Mix 2-[4-(4-fluorophenyl)-4-oxobutyl]-1,2,3,4,4a,5,7,8,9,10a-decahydro-4a,10a-trans-6H—cyclopenta[4,5]pyrrolo[2,3-g]isoquinolin-10(10H)—one, lactose, avicel and modified starch in a suitable mixer for 10–15 minutes. Add the magnesium stearate as a premix and mix for 4 minutes. Compress on a suitable press.

EXAMPLE 69

Tablet Formulation (Wet Granulation)

| Ingredients | mg/tablet | | | | |
|---|---|---|---|---|---|
| | 0.1 | 0.5 | 5.0 | 10.0 | 25.0 |
| 2-[4-(4-fluorophenyl)-4-oxobutyl]-1,2,3,4,4a,5,7,8,9,10a-decahydro-4a,10a-trans-6H—cyclopenta[4,5]pyrrolo[2,3-g]isoquinolin-10(10H)—one | 0.1 | 0.5 | 5.0 | 10.0 | 25.0 |

| Ingredients | mg/tablet | | | | |
|---|---|---|---|---|---|
| | 0.1 | 0.5 | 5.0 | 10.0 | 25.0 |
| Lactose | 103.9 | 103.5 | 99.0 | 148.0 | 197.0 |
| Modified Starch | 10.0 | 10.0 | 10.0 | 20.0 | 30.0 |
| Pregelatinized Starch | 10.0 | 10.0 | 10.0 | 20.0 | 30.0 |
| Magnesium Stearate | 1.0 | 1.0 | 1.0 | 2.0 | 3.0 |
| Total | 125 mg. | 125 mg. | 125 mg. | 200 mg. | 285 mg. |

Procedure:

Mix 2-[4-(4-fluorophenyl)-4-oxobutyl]-1,2,3,4,4a,5,7,8,9,10a-decahydro-4a,10a-trans-6H—cyclopenta[4,5]pyrrolo[2,3-g]isoquinolin-10(10H)—one, lactose, modified starch and pregelatinized starch in a suitable mixer, granulate with water. Dry, mill. Mix with the magnesium stearate and compress on a suitable press.

We claim:

1. A compound of the formula

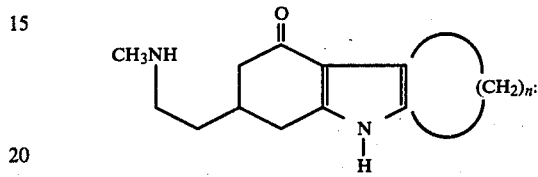

wherein n is 3, 4, 5 or 6.

* * * * *